(12) United States Patent
Kawano et al.

(10) Patent No.: US 8,168,412 B2
(45) Date of Patent: May 1, 2012

(54) METHOD FOR PRODUCING OPTICALLY-ACTIVE AMINE COMPOUND, RECOMBINANT VECTOR, AND TRANSFORMANT CONTAINING THE VECTOR

(75) Inventors: Shigeru Kawano, Takasago (JP); Noriyuki Ito, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 12/302,460

(22) PCT Filed: May 28, 2007

(86) PCT No.: PCT/JP2007/060806
§ 371 (c)(1),
(2), (4) Date: Nov. 25, 2008

(87) PCT Pub. No.: WO2007/139055
PCT Pub. Date: Dec. 6, 2007

(65) Prior Publication Data
US 2009/0148899 A1 Jun. 11, 2009

(30) Foreign Application Priority Data
May 29, 2006 (JP) ................................. 2006-148623

(51) Int. Cl.
*C12P 13/00* (2006.01)
(52) U.S. Cl. ...................................................... 435/128
(58) Field of Classification Search .................. None
See application file for complete search history.

(56) References Cited

U.S. PATENT DOCUMENTS

| | | | |
|---|---|---|---|
| 4,102,746 A * | 7/1978 | Goldberg | 435/96 |
| 5,126,256 A * | 6/1992 | Ebeling et al. | 435/190 |
| 6,197,558 B1 | 3/2001 | Fotheringham | |
| 6,346,402 B1 | 2/2002 | Iwasaki et al. | |
| 6,485,947 B1 * | 11/2002 | Rajgarhia et al. | 435/139 |
| 7,432,095 B2 * | 10/2008 | Nanba et al. | 435/190 |
| 2002/0192786 A1 * | 12/2002 | Yamada et al. | 435/193 |
| 2003/0046984 A1 * | 3/2003 | Jiang et al. | 73/53.03 |

FOREIGN PATENT DOCUMENTS

| | | |
|---|---|---|
| EP | 1449923 A1 * | 8/2004 |
| EP | 1 818 411 A1 | 8/2007 |
| JP | 7-85718 B2 | 9/1995 |
| WO | WO-87/01727 A1 | 3/1987 |
| WO | WO-91/05870 A1 | 5/1991 |
| WO | WO-98/48030 | 10/1998 |
| WO | WO-00/26351 A1 | 11/2000 |

OTHER PUBLICATIONS

Yamane et al. Enhanced cell-free protein synthesis using a S30 extract from *Escherichia coli* grown rapidly at 42 degrees C in an amino acid enriched medium. Biotechnol. Prog. (2005) 21, 608-613.*
Ozawa et al. Cell-free synthesis of N-labled protein for NMR studies. IUBMB Life (Sep. 2005) 57(9), 615-622.*
Shin et al., Biotechnol. Bioeng., 1999, vol. 65, No. 2, p. 206-211.
Shaked et al., J. Am. Chem. Soc., 1980, vol. 102, No. 23, p. 7104-7105.
Lin et al., J. Biosci. Bioeng., 1999, vol. 87, No. 3, p. 361-364.
Matcham et al., Chimia, vol. 53, 1999, pp. 584-589.
Taylor et el., Trends in biotechnology, vol. 16, 1998, pp. 412-418.
Soda K et al., "Production of D-amino acids—by converting . . . " WPI/Thomson, vol. 1995 No. 42, Sep. 10, 1987, XP002505787.
Yun H et al., "Sirnultaneous synthesis of enantiomerically . . . " Biotechnology Letters, vol. 25 No. 10, May 1, 2003; pp. 809-814, XP002420353.
European Search Report mailed Oct. 6, 2009 in connection with European Application No. 07744240.8.
English Translation of International Preliminary Report on Patentability (IPRP), Form PCT/IB/373 issued Dec. 10, 2008 for PCT/JP2007/060806.
English Translation of Written Opinion of the International Searching Authority, Form PCT/ISA/237 issued Dec. 10, 2008 for PCT/JP2007/060806.
Form PCT/IB/338 issued on Jan. 15, 2009.

* cited by examiner

*Primary Examiner* — Nashaat Nashed
(74) *Attorney, Agent, or Firm* — Birch, Stewart, Kolasch and Birch, LLP

(57) ABSTRACT

The present invention relates to a method for producing an optically-active amine compound. The method is characterized by using a transaminase (A), an α-keto acid reductase (B), and an enzyme (C), each having specific properties, in an identical reaction system to convert a ketone compound into a corresponding optically-active amine compound in which a carbon atom with an amino group bonded thereto serves as an asymmetric point. The present invention also relates to a recombinant vector for use in the method. The present invention makes it possible to efficiently produce an optically-active amine compound.

12 Claims, 4 Drawing Sheets

METHOD FOR PRODUCING OPTICALLY-ACTIVE AMINE COMPOUND, RECOMBINANT VECTOR, AND TRANSFORMANT CONTAINING THE VECTOR

TECHNICAL FIELD

The present invention relates to a method for producing an optically-active amine compound. The present invention also relates to a recombinant vector and a transformant containing the vector, each for use in the method for producing an optically-active amine compound.

BACKGROUND ART

An optically-active amino compound is a compound that is very useful as a synthetic intermediate for various medicines and pesticides.

A large number of methods for producing an optically-active amine compound with use of a transaminase, especially of methods for producing an optically-active α-amino acid, have been reported. An amination reaction catalyzed by a transaminase is a reversible reaction (equilibrium reaction). Therefore, in order to obtain a desired amine compound in good yield, it is necessary to bias the equilibrium reaction toward production of the desired amine compound. This is achieved, for example, by a method that involves the removal of a by-product compound from the reaction system. A number of such methods have been reported.

Examples of a method for producing an optically-active α-amino acid through amination of an α-keto acid with use of a transaminase are as follows:

(1) A method, using coupled aminotransferases, which biases equilibrium in reaction by removing a by-product α-keto acid (Patent Document 1: International Publication No. WO 87/01727 Pamphlet);

(2) A method, using an L-asparagine acid as an amino donor, which biases equilibrium in reaction by causing an acetolactate synthase to act on a pyruvic acid produced through chemical decarbonization of by-product oxaloacetate (Patent Document 2: Japanese Translation of PCT Patent Application Publication No. 514921/2002 (Tokuhyo 2002-514921));

(3) A method, using a D-amino acid as an amino donor, which biases equilibrium in reaction by causing an amino-acid dehydrogenase, an amino-acid racemase, and the like to act on a by-product α-keto acid to convert the α-keto acid into a D-amino acid serving as an amino donor (Patent Document 3: Japanese Examined Patent Application Publication No. 85718/1995 (Tokukohei 7-85718)); and (4) A method, using DL-alanine as an amino donor, which biases equilibrium in reaction by causing a lactate dehydrogenase and an expensive NADH to act on a by-product pyruvic acid to convert the pyruvic acid into a lactic acid (Patent Document 4: International Publication No. WO 91/05870 Pamphlet).

The above methods (1) to (3) are also described in *Trends biotechnol.*, 16, 412-418 (1998) (Non-patent Document 1).

Further, examples of a method for producing an optically-active amine compound other than an optically-active α-amino acid with use of a transaminase are as follows:

(a) A method, using a cell-free extract of microorganisms *Vibrio fluvialis*, which, during an amination reaction of acetophenone with use of L-alanine as an amino donor, biases equilibrium in reaction by causing a lactate dehydrogenase and an expensive NADH to act on a by-product pyruvic acid to convert the pyruvic acid into a lactic acid (Non-patent Document 2: *Biotechnol. Bioeng.*, 65(2), 206-211 (1999)); and (b) A method that, during production of (S)-methoxyisopropylamine with use of 2-aminopropane as an amino donor, biases equilibrium in reaction by removing by-product acetone from the reaction system through an increase in reaction temperature (Non-patent Document 3: *Chimia*, 53(12), 584-589 (1999)).

In Non-patent Document 2 described above in (a), the authors conclude that: A reaction that involves the conjugation of a lactate dehydrogenase to a cell-free extract requires an NADH regeneration system, and the addition of another enzyme complicates the reaction system; therefore, a reaction that involves the use of viable bacteria of *Vibrio fluvialis* is superior. Thus, the authors of Non-patent Document 2, who are skilled in the art, hold a negative view on a reaction that involves a combination of a transaminase, a lactate dehydrogenase, and a coenzyme regeneration system.

Patent Document 1: International Publication No. WO 87/01727 Pamphlet

Patent Document 2: Japanese Translation of PCT Patent Application Publication No. 514921/2002 (Tokuhyo 2002-514921)

Patent Document 3: Japanese Examined Patent Application Publication No. 85718/1995 (Tokukohei 7-85718)

Patent Document 4: International Publication No. WO 91/05870 Pamphlet

Non-patent Document 1: *Trends biotechnol.*, 16, 412-418 (1998)

Non-patent Document 2: *Biotechnol. Bioeng.*, 65(2), 206-211 (1999)

Non-patent Document 3: *Chimia*, 53(12), 584-589 (1999)

DISCLOSURE OF THE INVENTION

Problems to be Solved by the Invention

It is an object of the present invention to provide a method for efficiently producing an optically-active amino compound. Further, it is another object of the present invention to provide a recombinant vector and a transformant containing the vector, each for use in the method.

Means to Solve the Problems

As a result of diligent study to solve the foregoing problems, the inventors have found that the concomitant use of a transaminase having specific properties and two types of reductase each having specific properties makes it possible that a corresponding optically-active amine compound in which a carbon atom with an amino group bonded thereto serves as an asymmetric point is produced in good yield from a ketone compound without use of an expensive compound such as NADH. Thus, the inventors have finally come up with the present invention.

[1] A feature of the present invention is a method for producing an optically-active amine compound by using the following enzymes (A) to (C) in an identical reaction system to convert a ketone compound into a corresponding optically-active amine compound in which a carbon atom with an amino group bonded thereto serves as an asymmetric point:

(A) a transaminase, using an α-amino acid as an amino-group donor, which has an ability to act on the ketone compound to convert the ketone compound into the optically-active amine compound;

(B) an α-keto acid reductase, using a reduced β-nicotinamide adenine dinucleotide (NADH) or a reduced β-nicotinamide adenine dinucleotide phosphate (NADPH) as a coenzyme, which has an ability to reduce, to an α-hydroxy acid, an α-keto acid produced from the α-amino acid through action of the transaminase (A) and which does not act on the ketone compound; and (C) an enzyme that has an ability to convert, into NADH, an oxidized β-nicotinamide adenine dinucleotide (NAD$^+$) produced from the NADH through action of the α-keto acid reductase (B) or that has an ability to convert, into NADPH, an oxidized β-nicotinamide adenine dinucleotide phosphate (NADP$^+$) produced from the NADPH through action of the α-keto acid reductase (B).

[2] A feature of the present invention is the method, wherein the enzymes (A) to (C) are the following enzymes (A') to (C'), respectively:

(A') a transaminase, using α-alanine as an amino-group donor, which has an ability to act on a ketone compound to convert the ketone compound into a corresponding optically-active amine compound in which a carbon atom with an amino group bonded thereto serves as an asymmetric point;

(B') an α-keto acid reductase, using a reduced β-nicotinamide adenine dinucleotide (NADH) as a coenzyme, which has an ability to reduce, to a lactic acid, a pyruvic acid produced from the α-alanine through action of the transaminase (A') and which does not act on the ketone compound; and (C') an enzyme that has an ability to convert, into NADH, an oxidized β-nicotinamide adenine dinucleotide (NAD$^+$) produced from the NADH through action of the α-keto acid reductase (B).

[3] A feature of the present invention is the method, wherein a transformant obtained by introducing, into a host cell, DNA molecules respectively coding for the enzymes (A) to (C) or (A') to (C') and/or a product of culture thereof are/is each used as an enzyme source.

[4] A feature of the present invention is the method, wherein a transformant, obtained by transforming a host cell with use of either a plurality of recombinant vectors separately containing DNA molecules respectively coding for the enzymes (A) to (C) or (A') to (C'), or a single recombinant vector containing all the DNA molecules respectively coding for the enzymes (A) to (C) or (A') to (C'), which expresses the enzymes (A) to (C) or (A') to (C') in the same transformant and or a product of culture thereof are/is each used as an enzyme source.

[5] A feature of the present invention is the method, wherein the enzyme (B) or (B') is a lactate dehydrogenase and the enzyme (C) or (C') is a glucose dehydrogenase or a formate dehydrogenase.

[6] A feature of the present invention is the method, wherein the enzyme (B) or (B') is an L-lactate dehydrogenase and the enzyme (C) or (C') is a glucose dehydrogenase.

[7] A feature of the present invention is the method, wherein the enzyme (B) or (B') is an enzyme derived from a microorganism belonging to *Pediococcus acidilactici*.

[8] A feature of the present invention is the method, wherein the enzyme (C) or (C') is an enzyme derived from a microorganism belonging to *Bacillus megaterium* or *Thiobacillus* sp.

[9] A feature of the present invention is the method, wherein the transaminase (A) or (A') is an enzyme derived from a microorganism belonging to the genus *Pseudomonas* or the genus *Arthrobacter*.

[10] A feature of the present invention is the method, wherein the transaminase (A) or (A') is an enzyme derived from *Pseudomonas fluorescens* strain KNK08-18 (FERM BP-10599), *Pseudomonas* sp. strain KNK425 (FERM BP-6525), or *Arthrobacter* sp. strain KNK168 (FERM BP-5228).

[11] A feature of the present invention is the method, wherein the transaminase (A) or (A') is a polypeptide as set forth in any one of (a) to (c):

(a) a polypeptide consisting of an amino-acid sequence as set forth in SEQ ID NO: 1 of the Sequence Listing;

(b) a polypeptide consisting of an amino-acid sequence, as set forth in SEQ ID NO: 1 of the Sequence Listing, one or more amino acids of which are substituted, deleted, inserted, and/or added; and (c) a polypeptide consisting of an amino-acid sequence sharing 85% or higher homology with an amino-acid sequence as set forth in SEQ ID NO: 1 of the Sequence Listing.

[12] A feature of the present invention is the method, wherein the transaminase (A) or (A') is a polypeptide coded for by a polynucleotide as set forth in (1) or (2):

(1) a polynucleotide consisting of a base sequence as set forth in SEQ ID NO: 2 of the Sequence Listing; and (2) a polynucleotide that, under stringent conditions, hybridizes with DNA consisting of a base sequence as set forth in SEQ ID NO: 2 of the Sequence Listing.

[13] A feature of the present invention is the method, wherein the transaminase (A) or (A') is a polypeptide as set forth in any one of (d) to (f):

(d) a polypeptide consisting of an amino-acid sequence as set forth in SEQ ID NO: 6 of the Sequence Listing;

(e) a polypeptide consisting of an amino-acid sequence, as set forth in SEQ ID NO: 6 of the Sequence Listing, one or more amino acids of which are substituted, deleted, inserted, and/or added; and (f) a polypeptide consisting of an amino-acid sequence sharing 85% or higher homology with an amino-acid sequence as set forth in SEQ ID NO: 6 of the Sequence Listing.

[14] A feature of the present invention is the method, wherein the transaminase (A) or (A') is a polypeptide coded for by a polynucleotide as set forth in (3) or (4):

(3) a polynucleotide consisting of a base sequence as set forth in SEQ ID NO: 5 of the Sequence Listing; and (4) a polynucleotide that, under stringent conditions, hybridizes with DNA consisting of a base sequence as set forth in SEQ ID NO: 5 of the Sequence Listing.

[15] A feature of the present invention is the method, wherein the transaminase (A) or (A') is a polypeptide as set forth in any one of (g) to (i):

(g) a polypeptide consisting of an amino-acid sequence as set forth in SEQ ID NO: 25 of the Sequence Listing;

(h) a polypeptide consisting of an amino-acid sequence, as set forth in SEQ ID NO: 25 of the Sequence Listing, one or more amino acids of which are substituted, deleted, inserted, and/or added; and (i) a polypeptide consisting of an amino-acid sequence sharing 85% or higher homology with an amino-acid sequence as set forth in SEQ ID NO: 25 of the Sequence Listing.

[16] A feature of the present invention is the method, wherein the transaminase (A) or (A') is a polypeptide coded for by a polynucleotide as set forth in (5) or (6):

(5) a polynucleotide consisting of a base sequence as set forth in SEQ ID NO: 26 of the Sequence Listing; and (6) a polynucleotide that, under stringent conditions, hybridizes with DNA consisting of a base sequence as set forth in SEQ ID NO: 26 of the Sequence Listing.

[17] A feature of the present invention is the method as set forth in the numbered paragraphs above, wherein the ketone compound is represented by general formula (1)

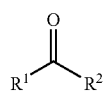
(1)

(where $R^1$ and $R^2$ are each a substitutable alkyl group, a substitutable aralkyl group, or a substitutable aryl group, are allowed to be bonded to each other to form a ring, but are different in structure) and the corresponding optically-active amino compound is represented by general formula (2)

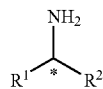
(2)

(where $R^1$ and $R^2$ are as defined in general formula (1) and the mark * indicates an asymmetric carbon atom).

[18] A feature of the present invention is the method, wherein the ketone compound is represented by general formula (3)

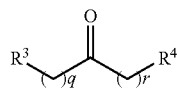
(3)

(where $R^3$ and $R^4$ are each a substitutable C6-C14 aryl group, C4-C14 heteroaryl group, C6-C14 aryloxy group, C4-C14 heteroaryloxy group, C1-C5 alkoxy group, C2-C5 alkoxycarbonyl group, C3-C5 branched-chain alkyl group, C2-C5 alkenyl group, C2-C5 alkynyl group, C5-C7 cycloalkyl group, methyl group, or carboxyl group; q is an integer of 0 to 7, r is an integer of 0 to 2; and q≧r, excluding a case where $R^3$ and $R^4$ are identical and q=r, $R^3$ not being a carboxyl group when q=0, $R^4$ not being a carboxyl group when r=0) and the corresponding optically-active amino compound is represented by general formula (4)

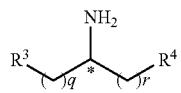
(4)

(where $R^3$, $R^4$, q, and r are as defined in general formula (3) and the mark * indicates an asymmetric carbon atom).

[19] A feature of the present invention is the method, wherein in general formulae (3) and (4), $R^4$ is a methyl group substitutable by a substituent selected from the group consisting of a halogen atom, a nitro group, a hydroxyl group, and a carboxyl group and r is 0 or 1.

[20] A feature of the present invention is the method, wherein in general formulae (3) and (4), $R^4$ is a methyl group and r=0.

[21] A feature of the present invention is the method, wherein in general formulae (3) and (4), q is an integer of 0 to 5 and $R^3$ is an aryl group substitutable by a substituent selected from the group consisting of a halogen atom, a nitro group, a hydroxyl group, a cyano group, a C1-C3 alkyl group, a C1-C3 alkoxy group, and a trifluoromethyl group.

[22] A feature of the present invention is the method, wherein in general formulae (3) and (4), q is an integer of 0 to 5 and $R^3$ is a group selected from the group consisting of a methyl group, a methoxy group, an ethoxy group, a phenyl group, a 2-chlorophenyl group, a 3-chlorophenyl group, a 4-chlorophenyl group, a 2-hydroxyphenyl group, a 3-hydroxyphenyl group, a 4-hydroxyphenyl group, a 2-methoxyphenyl group, a 3-methoxyphenyl group, a 4-methoxyphenyl group, a 3,4-dimethoxyphenyl group, a 2-trifluoromethylphenyl group, a 3-trifluoromethylphenyl group, a 4-trifluoromethylphenyl group, a pyridyl group, and a pyrazyl group.

[23] A feature of the present invention is the method, wherein the ketone compound is represented by general formula (5)

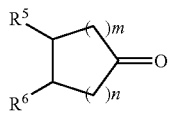
(5)

(where m is an integer of 0 to 2, n is an integer of 2 to 5 (n>m); $R^5$ and $R^6$ are each a halogen atom, a nitro group, a hydroxyl group, a cyano group, an amino group, a carboxyl group, a hydrogen atom, a C6-C14 aryl group, a C4-C14 heteroaryl group, a C6-C14 aryloxy group, a C4-C14 heteroaryloxy group, a C1-C8 alkyl group, a C1-C5 alkoxy group, a C1-C5 alkoxycarbonyl group, a C3-C5 branched-chain alkyl group, a C2-C5 alkenyl group, a C2-C8 alkynyl group, or a C5-C7 cycloalkyl group, each being allowed to have a substituent; and $R^5$ and $R^6$ are allowed to be bonded to each other to form a monocyclic or polycyclic hydrocarbon or a monocyclic or polycyclic heterocycle and are each allowed to have a substituent) and the corresponding optically-active amino compound is represented by general formula (6)

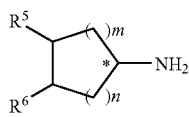
(6)

(where $R^5$, $R^6$, m, and n are as defined in general formula (5) and the mark * indicates an asymmetric carbon atom).

[24] A feature of the present invention is the method, wherein in general formulae (5) and (6), $R^5$ and $R^6$ are bonded to each other to form a substitutable benzene ring.

[25] A feature of the present invention is the method, wherein general formulae (5) and (6) each have a combination of m=1 and n=2, a combination of m=0 and n=3, or a combination m=0 and n=2.

[26] A feature of the present invention is the method, wherein optically-active amino compound is represented by general formula (6) is 1-aminotetraline, 2-aminotetraline, 5-methoxy-2-aminotetraline, 6-methoxy-2-aminotetraline, 7-methoxy-2-aminotetraline, 8-methoxy-2-aminotetraline, or 1-aminoindane.

[27] A feature of the present invention is the method, wherein the ketone compound is represented by general formula (7)

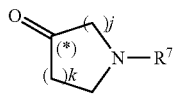
(7)

(where j and k are each an integer of 1 to 3 (k≧j); $R^7$ is a hydrogen atom, a C6-C14 aryl group, a C4-C14 heteroaryl group, a C1-C6 alkyl group, a C1-C6 alkoxy group, a C2-C15 acyl group, a C1-C6 alkoxycarbonyl group, a C7-C15 aralkyl group, a C8-C16 aralkyloxycarbonyl group, or a sulfonyl group substituted by a C1-C6 alkyl group or a C6-C14 aryl group) and the corresponding optically-active amino compound is represented by general formula (8)

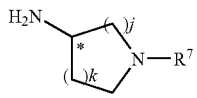
(8)

(where j, k, and $R^7$ are as defined in general formula (7) and the mark * indicates an asymmetric carbon atom).

[28] A feature of the present invention is the method, wherein general formulae (7) and (S) each contain a combination of k=1 and j=1 or a combination of k=2 and j=1.

[29] A feature of the present invention is the method, wherein in general formulae (7) and (8), $R^7$ is a group selected from the group consisting of a hydrogen atom, a phenyl group, a benzyl group, a benzoyl group, a benzyloxycarbonyl group, a t-butyloxycarbonyl group, an ethoxycarbonyl group, a methoxycarbonyl group, a mesyl group, and a tosyl group.

[30] A feature of the present invention is a recombinant vector containing DNA molecules respectively coding for the following enzymes (A) to (C):

(A) a transaminase, using an α-amino acid as an amino-group donor, which has an ability to act on the ketone compound to convert the ketone compound into the corresponding optically-active amine compound in which a carbon atom with an amino group bonded thereto serves as an asymmetric point;

(B) an α-keto acid reductase, using a reduced β-nicotinamide adenine dinucleotide (NADH) or a reduced β-nicotinamide adenine dinucleotide phosphate (NADPH) as a coenzyme, which has an ability to reduce, to an α-hydroxy acid, an α-keto acid produced through action of the transaminase (A'') and which does not act on the ketone compound; and (C) an enzyme that has an ability to convert, into NADH, an oxidized β-nicotinamide adenine dinucleotide ($NAD^+$) produced from the NADH through action of the α-keto acid reductase (B) or that has an ability to convert, into NADPH, an oxidized β-nicotinamide adenine dinucleotide phosphate ($NADP^+$) produced from the NADPH through action of the α-keto acid reductase (B).

[31] A feature of the present invention is the recombinant vector, wherein the enzymes (A) to (C) are the following enzymes (A') to (C'):

(A') a transaminase, using α-alanine as an amino-group donor, which has an ability to act on a ketone compound to convert the ketone compound into a corresponding optically-active amine compound in which a carbon atom with an amino group bonded thereto serves as an asymmetric point;

(B') an α-keto acid reductase, using a reduced β-nicotinamide adenine dinucleotide (NADH) as a coenzyme, which has an ability to reduce, to a lactic acid, a pyruvic acid produced from the α-alanine through action of the transaminase (A') and which does not act on the ketone compound; and (C') an enzyme that has an ability to convert, into NADH, an oxidized β-nicotinamide adenine dinucleotide ($NAD^+$) produced from the NADH through action of the α-keto acid reductase (B').

[32] A feature of the present invention is the recombinant vector, wherein the enzyme (B) or (B') is a lactate dehydrogenase and the enzyme (C) or (C') is a glucose dehydrogenase or a formate dehydrogenase.

[33] A feature of the present invention is the recombinant vector, wherein the reductase (B) or (B') is an L-lactate dehydrogenase and the reductase (C) or (C') is a glucose dehydrogenase.

[34] A feature of the present invention is the recombinant vector, wherein the enzyme (B) or (B') is an enzyme derived from a microorganism belonging to *Pediococcus acidilactici*.

[35] A feature of the present invention is the recombinant vector, wherein the enzyme (C) or (C') is an enzyme derived from a microorganism belonging to *Bacillus megaterium* or *Thiobacillus* sp.

[36] A feature of the present invention is the recombinant vector, wherein the enzyme (A) or (A') is an enzyme derived from a microorganism belonging to the genus *Pseudomonas* or the genus *Arthrobacter*.

[37] A feature of the present invention is the recombinant vector, wherein the enzyme (A) or (A') is an enzyme derived from *Pseudomonas fluorescens* strain KNK08-18 (FERM BP-10599), *Pseudomonas* sp. strain KNK425 (FERM BP-6525), or *Arthrobacter* sp. strain KNK168 (FERM BP-5228).

[38] A feature of the present invention is the recombinant vector, wherein the enzyme (A) or (A') is a polypeptide as set forth in SEQ ID NO: 1, SEQ ID NO: 6, or SEQ ID NO: 25 of the Sequence Listing.

[39] A feature of the present invention is a transformant obtained by transforming a host cell with use of the recombinant vector.

[40] A feature of the present invention is the transformant, wherein the host cell is *Escherichia coli*.

[41] A feature of the present invention is a method for producing a mixture of enzymes (A) to (C) or (A') to (C'), the method comprising the steps of: culturing the transformant in a culture medium; and accumulating the enzymes (A) to (C) or (A') to (C') in the culture medium and/or the transformant.

The other features of the present invention and the advantages thereof will be made clear by the descriptions and the drawings below in the specification.

Effects of the Invention

The present invention provides a method for efficiently producing an optically-active amino compound. The present invention also provides a recombinant vector and a transformant having the vector, each for use in the method.

BEST MODE FOR CARRYING OUT THE INVENTION

Figure 1:
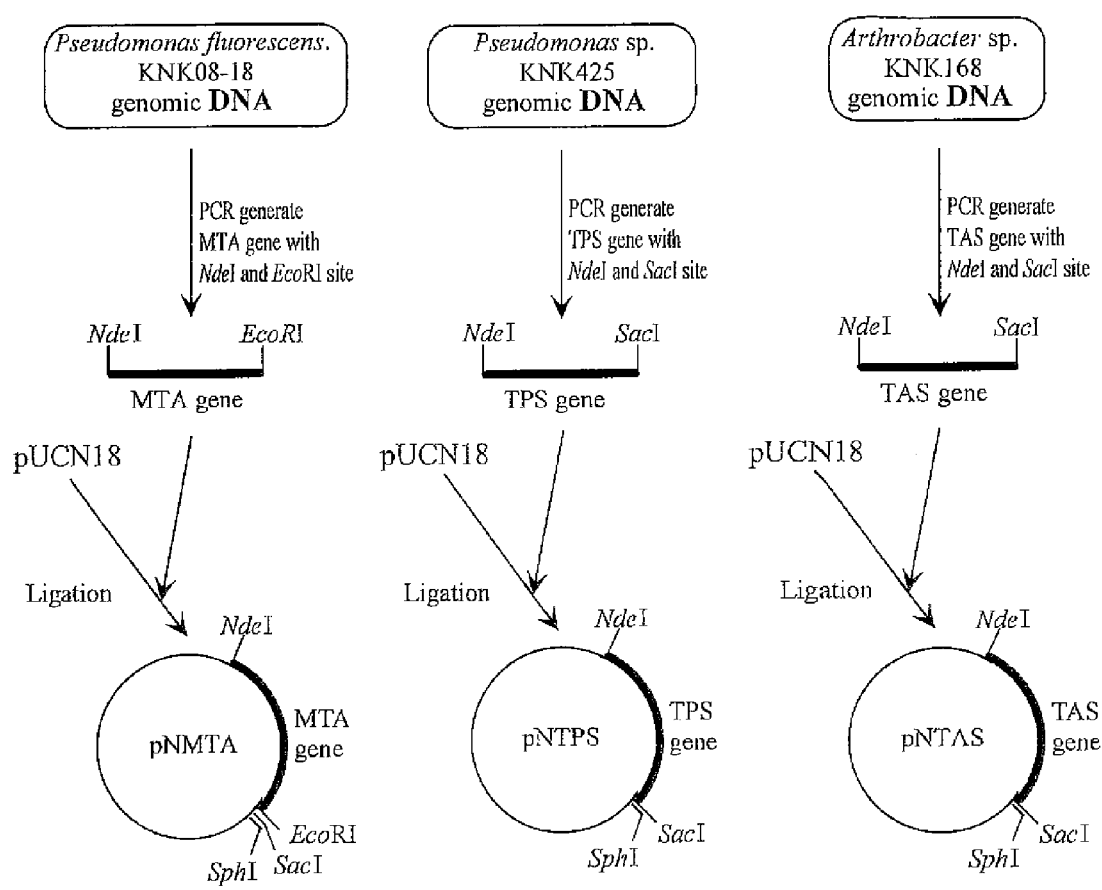
FIG. 1 is a schematic diagram of respective procedures for building recombinant plasmids pNMTA, pNTPS, and pNTAS.

In the following, the present invention will be detailed with reference to the following embodiments. However, the present invention is not limited to these embodiments.

Unless otherwise specified, isolation of DNA, preparation of a vector, genetic manipulation such as transformation that are described in the present specification can be performed according to methods described in published books such as *Molecular Cloning 2nd Edition* (Cold Spring Harbor Laboratory, 1989) and *Current Protocols in Molecular Biology* (Greene Publishing Associates and Wiley-Interscience). Unless otherwise specified, "%" used for description in the present specification means "% (w/v)".

1. Method for Producing an Optically-active Amine Compound

The present invention is a method for producing an optically-active amine compound in good yield by using the following enzymes (A) to (C) in an identical reaction system to efficiently convert a ketone compound into a corresponding optically-active amine compound in which a carbon atom with an amino group bonded thereto serves as an asymmetric point:

(A) a transaminase, using an α-amino acid as an amino-group donor, which has an ability to act on the ketone compound to convert the ketone compound into the optically-active amine compound;

(B) an α-keto acid reductase, using a reduced β-nicotinamide adenine dinucleotide (NADH) or a reduced β-nicotinamide adenine dinucleotide phosphate (NADPH) as a coenzyme, which has an ability to reduce, to an α-hydroxy acid, an α-keto acid obtained from the α-amino acid through action of the transaminase (A) and which does not act on the ketone compound; and (C) an enzyme that has an ability to convert, into NADH, an oxidized β-nicotinamide adenine dinucleotide (NAD$^+$) converted from the NADH through action of the α-keto acid reductase (B) or that has an ability to convert, into NADPH, an oxidized β-nicotinamide adenine dinucleotide phosphate (NADP$^+$) converted from the NADPH through action of the α-keto acid reductase (B).

The transaminase (A) stereoselectively transfers the amino group of the α-amino acid, which serves as an amino-group donor, to the ketone compound, thereby producing the α-keto acid, which is a product of deamination of the α-amino acid, and the optically-active amino compound, which is a product of amination of the ketone compound. In general, the reaction catalyzed by the transaminase (A) is a reversible reaction (equilibrium reaction). Therefore, the reaction stops under specific conditions where the four compounds, namely the α-amino acid, the α-keto acid, the ketone compound, and the optically-active amine compound are mixed in the reaction system, with the result that not all the ketone compound added is converted into the corresponding optically-active amine compound. For this reason, the molar quantity of the amine compound produced from the ketone compound added is low. This causes a problem of productivity with industrial production.

Further addition of the α-keto acid reductase (B), which has an ability to reduce the α-keto acid, i.e., the product, to an α-hydroxy acid makes it possible to reduce the concentration of the α-keto acid in the reaction system. This makes it possible to bias the transamination reaction toward production of the amine compound.

The reductive reaction of the α-keto acid by the α-keto acid reductase (B) absolutely needs the coenzyme NADH or NADPH. The addition of the enzyme (C), which has an ability to convert NAD$^+$ or NADP$^+$ into NADH or NADPH, makes it possible to regenerate the coenzyme. With this, the reductive reaction of the α-keto acid by the α-keto acid reductase (B) is accelerated.

As described above, the action of the enzymes (B) and (C) is absolutely necessary for equilibrium in the amination reaction catalyzed by the transaminase (A) to be biased toward the product. That is, it is not until the three enzymes (A) to (C) are used in cooperation with one another in an identical reaction system that an optically-active amine compound can be produced in good yield. This makes it possible to achieve improvement in productivity.

Optically-active amine compounds that can be produced by the present method will be detailed later.

In cases where the α-keto acid reductase (B) uses NADH as a coenzyme, an enzyme which has an ability to convert NAD$^+$ into NADH is used as the enzyme (C). Alternatively, in cases where the α-keto acid reductase (B) uses NADPH as a coenzyme, an enzyme which has an ability to convert NADP$^+$ into NADPH is used as the enzyme (C).

The enzymes (A) to (C) are preferably the following enzymes (A') to (C'):

(A') a transaminase, using α-alanine as an amino-group donor, which has an ability to act on a ketone compound to convert the ketone compound into a corresponding optically-active amine compound in which a carbon atom with an amino group bonded thereto serves as an asymmetric point;

(B') an α-keto acid reductase, using a reduced β-nicotinamide adenine dinucleotide (NADH) as a coenzyme, which has an ability to reduce, to a lactic acid, a pyruvic acid obtained from the α-alanine through action of the transaminase (A') and which does not act on the ketone compound; and (C') an enzyme that has an ability to convert, into NADH, an oxidized β-nicotinamide adenine dinucleotide (NAD$^+$) converted from the NADH through action of the α-keto acid reductase (B').

2. Three Types of Enzyme for Use in the Reaction

In the following, the enzymes (A) to (C) for use in the reaction will be detailed.

The enzymes (A) to (C) for use in the reaction may be microorganism-derived enzymes, animal-derived enzymes, or plant-derived enzymes. These enzymes are not particularly limited in purity or form as long as they have the desired activity. Examples of "enzymes" for use in the reaction of the present invention can take the form of purified enzymes or crude enzymes. Examples of "enzyme sources" for use in the reaction of the present invention can take various forms such as enzyme-containing substances, microbial culture fluids, products of culture, bacteria, culture fluids, recombinant microorganisms (transformants) having acquired the desired reaction activity through introduction of enzyme genes, and products of processing thereof. The term "products of processing" here means, for example, freeze-dried products, acetone-dried products, rubbed substances, autolyzed products, ultrasonic-ground substances, or alkali-treated substances. As long as the desired activity remains, the enzymes can be used in the reaction of the present invention. It is also possible to use commercially available enzymes or enzymes prepared by an experimenter.

Preferred forms of the enzymes (A) to (C) for use in the reaction are a transformant able to be obtained by introducing DNA molecules respectively coding for the enzymes (A) to (C) into a host cell and/or a product of culture thereof. Examples are as follows:

Three different transformants in which the enzymes (A) to (C) have been expressed respectively and/or products of culture thereof;

A transformant in which any two of the enzymes (A) to (C) have been expressed and/or a product of culture thereof and a transformant in which the remaining one of the enzymes (A) to (C) has been expressed and/or a product of culture thereof; and A transformant that expresses the enzymes (A) to (C) in the same cell and/or a product of culture thereof.

More preferred among the above is the transformant that expresses the enzymes (A) to (C) in the same transformant and/or the product of culture thereof.

The transformant that expresses the enzymes (A) to (C) in the same transformant can be obtained, for example, by preparing a single enzyme expression vector containing all the DNA molecules respectively coding for the enzymes (A) to (C) and by transforming a host cell with use of the enzyme expression vector, or can be obtained by transforming a host cell with use of a plurality of enzyme expression vectors separately containing the DNA molecules respectively coding for the enzymes (A) to (C).

The transformant thus obtained can be cultured with use of a normal liquid nutrient culture medium containing a carbon source, a nitrogen source, inorganic salts, organic nutrients, and the like, provided the transformant proliferates. Further, the culture temperature is generally 4° C. to 50° C., or preferably 20° C. to 40° C. The culture temperature may be adjusted in accordance with the amount of a desired enzyme that is expressed.

It should be noted that a method for transformation, a host-vector system, a method for expressing each enzyme gene, an enzyme expression vector will be detailed later.

3. Transaminase (A)

The following describes each of the enzymes (A) to (C).

The transaminase (A) encompasses any transaminase that uses α-alanine as an amino-group donor and has an ability to act on a ketone compound to convert the ketone compound into a corresponding optically-active amine compound in which a carbon atom with an amino group bonded thereto serves as an asymmetric point.

A method for determining whether the transaminase has the above physical and chemical properties will be described below with reference to an example where the amino-group donor is alanine and the ketone compound is acetophenone. The alanine, which serves as an amino-group donor, may be D-alanine, L-alanine, or DL-alanine, one of which that is perfect for the stereoselectivity of the transaminase to be evaluated is selected.

After the addition of acetophenone 1% and alanine 15% to an enzyme-containing solution and the adjustment of pH to 7.0, the resultant solution is stirred overnight at 30° C. After the pH of the reaction liquid obtained after the reaction is adjusted to not less than 11 with an aqueous solution of sodium hydroxide, the reaction liquid is mixed well with a solvent such as toluene. A part of the organic layer is analyzed under the following conditions for capillary column chromatographic analysis, whereby the production of phenethylamine is checked for.

[Conditions for Capillary Column Chromatographic Analysis]

Column: Rtx-5 Amine (30 m×0.25 mm ID) manufactured by Restek Corporation

Detection: FID

Carrier gas: helium (150 kPa)

Column temperature: 100° C.

Vaporizing chamber temperature: 250° C.

Elution time: phenethylamine 8.4 min., acetophenone 9.5 min.

Further, in cases where the production of phenethylamine is found out, the organic layer is mixed well with 1 N hydrochloric acid. A part of the aqueous layer is analyzed under the following conditions for high-performance liquid chromatographic analysis, whereby the optical purity of phenethylamine is checked.

[Conditions for High-performance Liquid Chromatographic Analysis]

Column: CROWNPAK CR(+) manufactured by Daicel Chemical Industries, Ltd.

Detection wavelength: 254 nm

Mobile phase: aqueous solution of perchloric acid (with a pH of 1.5)/methanol=85/15 (by volume)

Flow rate: 1.0 ml/min.

The results of these two analyses make it possible to easily determine whether or not the transaminase (A) has the above physical and chemical properties.

The method for determination can be similarly carried out also when the alanine is replaced by another α-amino acid. Further, the method for determination can be carried out also when the acetophenone is replaced by another ketone compound. In these cases, the other reaction conditions and the condition for analysis of an amine compound to be produced are appropriately adjusted separately according to need.

The transaminase (A) can be isolated from an organism that transfers the amino group of an α-amino acid to a ketone compound. The enzyme can be found in a microorganism, for example, in the following manner. After a microorganism is cultured in an appropriate culture medium and harvested, an α-amino acid and a ketone compound are allowed to react with each other in the presence of a nutrient such as glucose in buffer solution. After the reaction, it is only necessary that the production of an amine compound corresponding to the ketone compound be checked for by analyzing the reaction liquid by a known method such as high-performance liquid chromatography or gas chromatography. Further, since a reaction catalyzed by a transaminase is an equilibrium reaction, the transaminase (A) can also be isolated from a microorganism that transfers the amino group of an amine compound to an α-keto acid. After the same reaction has been performed as described above, it is only necessary that the production of an α-amino acid through amination of an α-keto acid be checked for. Usable examples of the culture medium in which a microorganism is cultured include a normal liquid nutrient culture medium containing a carbon source, a nitrogen source, inorganic salts, organic nutrients, and the like, provided the microorganism proliferates. The culture can be performed, for example, by shaking or aeration with a pH of 4 to 8 at a temperature of 25° C. to 37° C.

The transaminase (A) is not limited in origin. However, preferred examples of the origin of the transaminase (A) include a microorganism belonging to the genus *Pseudomonas* or the genus *Arthrobacter*. More preferred examples include *Pseudomonas fluorescens* strain KNK08-18 (FERM BP-10599), *Pseudomonas* sp. strain KNK425 (FERM BP-6525), and *Arthrobacter* sp. strain KNK168 (FERM BP-5228). The microorganisms specified above by Depository Nos. FERM BP-10599 (see Example 1 below), FERM BP-6525 (see Example 2), and FERM BP-5228 (Example 3) have been deposited at the International Patent Organism Depository of the National Institute of Advanced Industrial Science and Technology (Tsukuba Central 6, 1-1, Higashi 1-chome, Tsukuba-shi, Ibaraki-ken 305-8566 Japan).

The transaminase (A) encompasses any transaminase that uses α-amino acid as an amino-group donor and has an ability to convert a ketone compound into a corresponding optically-active amine compound in which a carbon atom with an amino group bonded thereto serves as an asymmetric point. However, the transaminase (A) is preferably a transaminase (A'), using α-alanine as an amino-group donor, which has an ability to act on a ketone compound to convert the ketone compound into a corresponding optically-active amine compound in which a carbon atom with an amino group bonded thereto serves as an asymmetric point. Examples of such an enzyme include: an (S)-α-phenethylamine-pyruvic acid transaminase described in International Publication No. WO 00/26351 Pamphlet; a polypeptide, described in claims 28 and 29 of International Publication No. WO 98/48030 Pamphlet, which has transaminase activity; and a polypeptide, coded for by the DNA of claim 23 of International Publication No. WO 98/48030 Pamphlet, which has transaminase activity.

Other examples include the following polypeptides (a) to (c):

(a) a polypeptide consisting of an amino-acid sequence as set forth in SEQ ID NO: 1 of the Sequence Listing;

(b) a polypeptide consisting of an amino-acid sequence, as set forth in SEQ ID NO: 1 of the Sequence Listing, one or more amino acids of which are substituted, deleted, inserted, and/or added; and (c) a polypeptide consisting of an amino-acid sequence sharing 85% or higher homology with an amino-acid sequence as set forth in SEQ ID NO: 1 of the Sequence Listing.

Further examples include a polypeptide coded for by the following polynucleotide (1) or (2):

(1) a polynucleotide consisting of a base sequence as set forth in SEQ ID NO: 2 of the Sequence Listing; or (2) a polynucleotide that, under stringent conditions, hybridizes with DNA consisting of a base sequence as set forth in SEQ ID NO: 2 of the Sequence Listing.

4. α-keto Acid Reductase (B)

The α-keto acid reductase (B) is a reductase that has such physical and chemical properties as to use a reduced β-nicotinamide adenine dinucleotide (NADH) or a reduced β-nicotinamide adenine dinucleotide phosphate (NADPH) as a coenzyme, to have an ability to reduce, to an α-hydroxy acid, an α-keto acid obtained from the α-amino acid through action of the transaminase (A), and not to act on the ketone compound, which serves as a substrate for the transaminase (A). The α-keto acid reductase (B) may be any reductase that has such activity.

The phrase "not to act on the ketone compound, which serves as a substrate for the transaminase (A)" here means that the activity with which the ketone compound, which serves as a substrate for the transaminase (A), is reduced is far less than the activity with which the α-keto acid obtained from the α-amino acid through action of the transaminase (A) is reduced to the α-hydroxy acid. Specifically, the values of activity with respect to the ketone compound and the α-keto acid are measured by an activity measurement method described below and compared with each other. In cases where the value of activity with respect to the ketone compound is not more than 1/100 of the value of activity with respect to the α-keto acid, the α-keto acid reductase (B) is judged as not acting on the ketone compound.

A method for determining whether the α-keto acid reductase (B) has the above physical and chemical properties will be described below with reference to an example where the coenzyme is NADH and the α-keto acid is a pyruvic acid.

The value of reduction activity with respect to the pyruvic acid can be calculated from the rate of diminution in absorbance at 340 nm of 3.0 ml of a reaction liquid in which a pyruvic acid 20 mM, NADH 0.25 mM, and 0.05 ml of enzyme solution have been reacted with 100 mM phosphate buffer solution (with a pH of 6) at 30° C. for three minutes.

The value of reduction activity with respect to the ketone compound can be measured by adding the ketone compound to the activity measurement system instead of adding the pyruvic acid.

The measurement of enzyme activity under both the conditions makes it possible to easily determine whether or not the enzyme has the above physical and chemical properties.

The method for determination can be performed through measurement also when the NADH is replaced by NADPH. Further, in cases where the pyruvic acid is replaced by another α-keto acid such as a hydroxypyruvic acid, α-keto acid reduction activity other than pyruvic acid reduction activity (e.g., hydroxypyruvic acid reduction activity) is determined. In this case, the other reaction conditions are appropriately adjusted separately according to need.

The α-keto acid reductase (B) can be isolated from an organism that has reduction activity with respect to an α-keto acid. The enzyme can be found in a microorganism, for example, in the following manner. After a microorganism is cultured in an appropriate culture medium, harvested, and then reacted with an α-keto acid in the presence of a nutrient such as glucose in buffer solution. After the reaction, it is only necessary to check for the production of an α-hydroxy acid by analyzing the reaction liquid by a known method such as high-performance liquid chromatography or gas chromatography. Usable examples of the culture medium in which a microorganism is cultured include a normal liquid nutrient culture medium containing a carbon source, a nitrogen source, inorganic salts, organic nutrients, and the like, provided the microorganism proliferates. The culture can be performed, for example, by shaking or aeration with a pH of 4 to 8 at a temperature of 25° C. to 37° C.

Since the α-keto acid reductase (B) reduces the α-keto acid and converts it to the α-hydroxy acid, it is preferable to select, as the α-keto acid reductase (B), an α-keto acid reductase unlikely to be inhibited by the α-hydroxy acid, i.e., the reaction product. Examples of such an α-keto acid reductase include an α-keto acid reductase obtainable from a microorganism selected from the group consisting of the genus *Lactobacillus*, the genus *Pediococcus*, the genus *Enterococcus*, and the genus *Achromobacter*. More specific examples include an α-keto acid reductase obtainable from a microorganism selected from *Lactobacillus helveticus, Lactobasillus acidophilus, Lactobacillus brevis, Pediococcus acidilactici, Pediococcus pentosaceus, Enterococcus faecalis*, and *Achromobacter xylosoxidans* subsp. *xylosoxidans*.

Still more specific examples include an α-keto acid reductase obtainable from a microorganism selected from the group consisting of *Lactobacillus helveticus* JCM1120, *Lactobasillus acidophilus* JCM 1132, *Lactobacillus brevis* JCM1059, *Pediococcus acidilactici* JCM8797, *Pediococcus*

*pentosaceus* JCM5890, *Enterococcus faecalis* JCMS803, and *Achromobacter xylosoxidans* subsp. *xylosoxidans* NBRC13495.

These microorganisms are available from various depository institutions to a person skilled in the art. Examples of the depository institutions include the following institutions:
RIKEN BioResource Center (those of the above microorganisms which are specified by JCM codes); and
NITE Biological Resource Center (those of the above microorganisms which are specified by NBRC codes).

The α-keto acid reductase (B) is preferably a reductase (B'), using a reduced β-nicotinamide adenine dinucleotide (NADH) as a coenzyme, which has an ability to reduce a pyruvic acid to a lactic acid and which does not act on the ketone compound, which serves as a substrate for the transaminase (A).

A more preferable example is an α-keto acid reductase such as an L- or D-lactate dehydrogenase, an L- or D-hydroxyisocaproate dehydrogenase, or an L- or D-mandelate dehydrogenase. A still more preferable example is a lactate dehydrogenase or, in particular, an L-lactate dehydrogenase (see Example 4 below). A more suitable example is an L-lactate dehydrogenase derived from a microorganism belonging to *Pediococcus acidilactici*. A still more suitable example is an L-lactate dehydrogenase (PALDH) derived from *Pediococcus acidilactici* JCM8797 (see Example 4).

5. Enzyme (C)

The enzyme (C) may be any enzyme that has an ability to convert an oxidized β-nicotinamide adenine dinucleotide ($NAD^+$) into NADH or that has an ability to convert an oxidized β-nicotinamide adenine dinucleotide phosphate ($NADP^+$) into NADPH (such an ability being hereinafter referred to as "coenzyme regenerating ability").

A method for determining whether the enzyme (C) has the coenzyme regenerating ability will be described below with reference to an example where NADH is used as a coenzyme and glucose is used as a substrate for the reduced compound.

The value of activity of reduction from $NAD^+$ to NADH can be calculated from the rate of increase in absorbance at 340 nm of 3.0 ml of a reaction liquid in which glucose 100 mM, $NAD^+$ 2 mM, and 0.05 ml of enzyme solution have been reacted with 1.0 M Tris-HCl buffer solution (with a pH of 8) at 30° C. for three minutes.

The measurement of enzyme activity under the present conditions makes it possible to easily determine whether or not the enzyme has the physical and chemical properties of the present invention, i.e., the coenzyme regenerating ability. The method for determination can be performed through measurement also when the $NAD^+$ is replaced by $NADP^+$. Further, the method for determination can be carried out also when the glucose is replaced by another substrate such as a formic acid. In this case, the other reaction conditions are appropriately adjusted separately according to need.

The enzyme (C) can be isolated from almost any organism. The enzyme can be found in a microorganism, for example, in the following manner. That is, it is only necessary to carry out the method for determination after preparing a cell-free extract by culturing a microorganism in an appropriate culture medium and harvesting it. Usable examples of the culture medium in which a microorganism is cultured include a normal liquid nutrient culture medium containing a carbon source, a nitrogen source, inorganic salts, organic nutrients, and the like, provided the microorganisms proliferate. The culture can be performed, for example, by shaking or aeration with a pH of 4 to 8 at a temperature of 25° C. to 37° C.

The enzyme (C) is preferably a reductase (C') that has an ability to convert an oxidized β-nicotinamide adenine dinucleotide ($NAD^+$) into NADH and does not act on the ketone compound, which serves as a substrate for the transaminase (A).

Examples of such an enzyme include a hydrogenase, a formate dehydrogenase, a glucose-6-phosphate dehydrogenase, and a glucose dehydrogenase. Suitably usable examples include a glucose dehydrogenase (see Example 4) and a formate dehydrogenase (see Example 28).

Examples of the formate dehydrogenase include enzymes obtainable from microorganisms such as the genus *Candida*, the genus *Kloeckera*, the genus *Pichia*, the genus *Lipomyces*, the genus *Pseudomonas*, the genus *MoTaxella*, the genus *Hyphomicrobium*, the genus *Paracoccus*, the genus *Thiobacillus*, and the genus *Ancylobacter* or, in particular, from *Thiobacillus* sp. (see Example 28).

Examples of the glucose dehydrogenase include enzymes obtainable from microorganisms such as the genus *Bacillus* or, in particular, from *Bacillus megaterium* (see Example 4).

6. Isolation of Each Enzyme from an Organism from Which the Enzyme Originates

The enzymes (A) to (C) of the present invention are isolated from the aforementioned organisms, respectively. The isolation of each enzyme can be carried out through an appropriate combination of protein purification techniques well known to a person skilled in the art. For example, the isolation of each enzyme can be carried out in the following manner. First, the corresponding microorganism is cultured in an appropriate culture medium, and the bacteria are collected from the culture fluid by centrifugation or filtration. The bacteria thus obtained are ground by an ultrasonic grinder or a physical method that involves the use of glass beads or the like. After that, the residual bacteria are removed by centrifugation. Thus obtained is a cell-free extract. Then, the enzyme of the present invention is isolated from the cell-free extract by using methods such as salting out (e.g., ammonium sulfate precipitation and sodium phosphate precipitation), solvent precipitation (fractional precipitation of protein by acetone or ethanol), dialysis, gel filtration chromatography, ion-exchange chromatography, reversed phase chromatography, and ultrafiltration alone or in combination.

7. Gene Cloning of Each Enzyme

Each of the DNA molecules respectively coding for the enzymes (A) to (C) may be any DNA molecule capable of expressing the corresponding enzyme in a host cell into which it has been introduced according to the after-mentioned method, and may contain any untranslated region. Once the enzyme is obtained, a person skilled in the art can use a publicly-known method to obtain such a DNA molecule from an organism from which the enzyme originates. For example, such a DNA molecule can be obtained in the following manner.

First, each of the enzymes (A) to (C) thus isolated is digested with use of an appropriate endopeptidase, and the resultant peptide fragment is batched off by reversed phase HPLC. Then, a part or all of the amino-acid sequence of the peptide fragment is determined, for example, by a Protein Sequencer ABI492 (manufactured by Applied Biosystems).

On the basis of the amino-acid sequence information thus obtained, a PCR (Polymerase Chain Reaction) primer for amplifying a part of the DNA coding for the polypeptide is synthesized. Next, the chromosome DNA of a microorganism from which the polypeptide originates is prepared by a normal DNA isolation technique such as a method taught by Visser et al. (*Appl. Microbiol. Biotechnol.*, 53, 415 (2000)). The aforementioned PCR primer is used to perform a PCR for which the chromosome DNA serves as a template, whereby a part of the DNA coding for the polypeptide is amplified and the base sequence thereof is determined. The base sequence is determined, for example, by a DNA Sequencer ABI373A (manufactured by Applied Bio systems).

Once a part of the base sequence of the DNA coding for the polypeptide is found out, all of the sequence can be determined, for example, by an Inverse PCR technique (*Nucl. Acids Res.*, 16, 8186 (1988)).

In cases where each of the DNA molecules respectively coding for the enzymes (A) to (C) has been isolated and a method for isolation thereof has been reported, the DNA of the desired enzyme can be obtained according to the method so described.

Examples of enzymatic DNA thus obtained, e.g., of DNA of the transaminase (A) include DNA containing a base sequence represented by SEQ ID NO: 2 of the Sequence Listing. Further, examples of the transaminase (A) include: a polypeptide, coded for by a base sequence represented by SEQ ID NO: 2 of the Sequence Listing, which consists of an amino-acid sequence represented by SEQ ID NO: 1 of the Sequence Listing; and a polypeptide, coded for by a base sequence represented by SEQ ID NO: 5 of the Sequence Listing, which consists of an amino-acid sequence represented by SEQ ID NO: 6 of the Sequence Listing.

The following describes the amino-acid sequence represented by SEQ ID NO: 1 of the Sequence Listing and the base sequence represented by SEQ ID NO: 2.

8. Amino-Acid Sequence of SEQ ID NO: 1 of the Sequence Listing

In addition to the polypeptide consisting of an amino-acid sequence represented by SEQ ID NO: 1 of the Sequence Listing, examples of the transaminase (A) may include a polypeptide that consists of an amino-acid sequence, represented by SEQ ID NO: 1 of the Sequence Listing, one or more (e.g., not more than 60, preferably not more than 20, more preferably not more than 15, still more preferably not more than 10, or still more preferably not more than 5, 4, 3, or 2) amino acids of which are substituted, deleted, inserted, and/or added, and that has the physical and chemical properties of the transaminase (A) as described above in Section "3. Transaminase (A)".

The polypeptide consisting of an amino-acid sequence, represented by SEQ ID NO: 1 of the Sequence Listing, one or more amino acids of which are substituted, deleted, inserted, and/or added can be prepared in conformity with a publicly-known method described, for example, in *Current Protocols in Molecular Biology* (John Wiley and Sons, Inc., 1989), and encompasses any polypeptide that has the activity of the transaminase (A).

Although there is no particular limitation on the location, in the amino-acid sequence represented by SEQ ID NO: 1 of the Sequence Listing, where an amino acid is substituted, deleted, inserted, and/or added, it is preferable to avoid a highly conserved region. The term "highly conserved region" here means a location where there is correspondence of amino acids among a plurality of sequences in cases where a plurality of enzymes of different origin are compared after optimally aligning amino-acid sequences thereof. A highly conserved region can be confirmed by using a tool such as GENETYX to make a comparison between the amino-acid sequence represented by SEQ ID NO: 1 and the amino-acid sequence of a transaminase derived from another microorganism described above.

An amino-acid sequence altered through substitution, insertion, deletion, and/or addition may contain only one type of alteration (e.g., substitution), or may contain two types of alteration (e.g., substitution and insertion).

Further, in the case of substitution, it is preferable that the substituting amino acid be an amino acid (homologous amino acid) having properties similar to those of the amino acid to be substituted. It should be noted here that those amino acids in the same one of the following groups are homologous amino acids:

(First group: neutral nonpolar amino acids) Gly, Ala, Val, Leu, Ile, Met, Cys, Pro, Phe;
(Second group: neutral polar amino acids) Ser, Thr, Gln, Asn, Trp, Tyr;
(Third group: acidic amino acids) Glu, Asp; and
(Fourth group: basic amino acids) His, Lys, Arg.

The number of amino acids that are substituted, deleted, inserted, and/or added is not particularly limited, provided the altered polypeptide has the activity of the transaminase (A). However, it is preferable to share 85% or higher sequence homology, more preferably 90% or higher sequence homology, still more preferably 95% or higher sequence homology, or most preferably 99% or higher sequence homology, with the amino-acid sequence represented by SEQ ID NO: 1 of the Sequence Listing. The sequence homology can be expressed by a value obtained by making a comparison between the amino-acid sequence represented by SEQ ID NO: 1 of the Sequence Listing and the altered amino-acid sequence as with the confirmation of a highly conserved region, by dividing the number of locations of correspondence of amino acids between the sequences by the total number of amino acids compared, and by multiplying the quotient by 100.

The amino-acid sequence represented by SEQ ID NO: 1 can have an additional amino-acid sequence bonded thereto, provided it has the activity of the transaminase (A). For example, a tag sequence such as a histidine tag or an HA tag can be added. Alternatively, the amino-acid sequence represented by SEQ ID NO: 1 may be fused with another protein to form a fusion protein. Further, the amino-acid sequence represented by SEQ ID NO: 1 may be a peptide fragment, provided it has the activity of the transaminase (A).

The same applies to the amino-acid sequence represented by SEQ ID NO: 6 of the Sequence Listing and an amino-acid sequence represented by SEQ ID NO: 25 of the Sequence Listing. See International Publication No. WO 98/48030 Pamphlet for a protein specified by the amino-acid sequence of SEQ ID NO: 25, a microorganism from which the protein is derived, and the mycological properties thereof.

9. Base Sequence of SEQ ID NO: 2 of the Sequence Listing

Examples of DNA coding for the transaminase (A) include DNA that, under stringent conditions, hybridizes with DNA consisting of a base sequence represented by SEQ ID NO: 2 of the Sequence Listing or DNA consisting of a base sequence complementary to the base sequence represented by SEQ ID NO: 2.

The term "DNA that, under stringent conditions, hybridizes with DNA consisting of a base sequence complementary to the base sequence represented by SEQ ID NO: 2" here means DNA that is obtained through a colony hybridization technique, a plaque hybridization technique, or a Southern hybridization technique under stringent conditions by using as a probe the DNA consisting of a base sequence complementary to the base sequence represented by SEQ ID NO: 2.

Hybridization can be performed in conformity with a method described, for example, in *Molecular Cloning, A Laboratory Manual*, Second Edition (Cold Spring Harbor Laboratory Press, 1989). Examples of the "DNA that hybridizes under stringent conditions" include DNA able to be obtained by performing hybridization at 65° C. in the presence of 0.7 to 1.0 M NaCl with use of a filter to which colony- or plaque-derived DNA has been immobilized and then washing the filter at 65° C. with 2×SSC solution (1×SSC solution is made up of 150 mM sodium chloride and 15 mM sodium citrate), preferably at 65° C. with a 0.5×SSC solution, more preferably at 65° C. with 0.2×SSC solution, or still more preferably at 65° C. with 0.1×SSC solution.

The hybridization conditions are not particularly limited to those described above. Possible factors that affect the stringency of hybridization include temperature and salt concentration. A person skilled in the art can achieve optimum stringency by appropriately selecting these factors.

Examples of DNA capable of hybridization under the above conditions include DNA sharing 70% or higher sequence homology, preferably 80% or higher, more preferably 85% or higher, still more preferably 90% or higher, even more preferably 95% or higher, or most preferably 99% or higher, with DNA represented by SEQ ID NO: 2, and encompass any DNA that codes for a polypeptide which has the activity of the transaminase (A).

The "sequence homology (%)" here is expressed by a numerical value obtained by optimally aligning two DNA molecules to be compared, by dividing the number of locations of correspondence of nucleic-acid bases (e.g., A, T, C, G, U, or I) between the sequences by the total number of bases compared, and by multiplying the quotient by 100.

The sequence homology can be calculated, for example, by using the following tools for analysis of sequences: GCG Wisconsin Package (Program Manual for the Wisconsin Package, Version 8, September 1994, Genetics Computer Group, 575 Science Drive Madison, Wis., USA 53711; Rice, P. (1996) Program Manual for EGCG Package, Peter Rice, Sanger Centre, Hinxton Hall, Cambridge, CB10 1RQ, England); and the ExPASy World Wide Web molecular biology server (Geneva University Hospital and the University of Geneva, Geneva, Switzerland).

The same applies to the base sequence represented by SEQ ID NO: 5 of the Sequence Listing and a base sequence represented by SEQ ID NO: 26 of the Sequence Listing. See International Publication No. WO 98/48030 Pamphlet for a protein specified by the amino-acid sequence of SEQ ID NO: 25, a microorganism from which the protein is derived, and the mycological properties thereof.

10. Host-Vector System

An enzyme expression vector can be prepared by inserting, into an expression vector, a polynucleotide coding for each of the enzymes (A) to (C). Further, each of the enzymes (A) to (C) can be expressed by culturing a transformant obtained by transforming a host organism with use of the enzyme expression vector.

In order to obtain a transformant that expresses each of the enzymes (A) to (C) in the same organism, it is only necessary to transform a host organism with use of an enzyme expression vector prepared by inserting, into a single expression vector, a polynucleotide coding for each of the enzymes (A) to (C). Further, for the purpose of avoiding incompatibility, the transformant that expresses each of the enzymes (A) to (C) in the same organism can also be obtained by preparing a plurality of enzyme expression vectors through separate insertion of polynucleotides into a plurality of vectors of different replication origin and transforming a host organism with use of these enzyme expression vectors. Furthermore, it is possible to use both of these transformants or a method that introduces, into a chromosome, a polynucleotide coding for each of the enzymes (A) to (C).

An expression vector to be used above is not particularly limited as long as it can express, in an appropriate host organism, a gene for which the corresponding DNA codes. Examples of such a vector include a plasmid vector, a phage vector, and a cosmid vector. Further usable examples include a shuttle vector capable of exchanging genes with another host strain.

Such a vector normally contains a control factor such as lacUV5 promoter, trp promoter, trc promoter, tac promoter, lpp promoter, tufB promoter, recA promoter, or pL promoter, for example, in the case of *Escherichia coli*, and can be suitably used as an expression vector that contains an expression unit operably linked to DNA of the present invention. Examples include pUCN18 (see Example 1), pSTV28 (produced by Takara Bio Inc.), and pUCNT (International Publication No. WO 94/03613 Pamphlet).

The term "control factor" used in the present specification means a functional promoter and a base sequence having a given related transcription element (such as an enhancer, a CCAAT box, a TATA box, or an SPI site).

The term "operably linked to" used in the present specification means that various regulatory elements, such as promoters and enhancers, which regulate the expression of genes and genes are linked so as to be operable in a host cell. It is well known to a person skilled in the art that the type of control factor can vary depending on the host.

Vectors, promoters, and the like usable in various organisms are detailed, for example, in *Biseibutsugaku Kiso Koza* 8 *Idenshi Kogaku* (*Genetic Engineering, Volume 8 of Basic Course on Molecular Biology*) (Kyoritsu Shuppan Co., Ltd., 1987).

A host organism to be used for expressing each enzyme is not particularly limited as long as it is an organism, transformed by an enzyme expression vector containing DNA coding for each enzyme, which can express an enzyme into which the DNA has been introduced. Usable examples of microorganisms include: bacteria, such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*, whose host-vector systems have been developed; *actinomyces*, such as the genus *Rhodococcus* and the genus *Streptomyces*, whose host-vector systems have been developed; yeast, such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida*, whose host-vector system has been developed; and fungi, such as the genus *Neurospora*, the genus *Aspergillus*, the genus *Cephalosporium*, and the genus *Trichoderma*, whose host-vector systems have been developed. Further, other than host-vector systems in microorganisms, various host-vector systems in plants and animals have been developed. In particular, a system that expresses a large amount of foreign protein in an insect (Nature 315, 592-594 (1985)) such as a silkworm or in a plant such as canola, corn, or potato is being developed, and can be suitably used. Among these, *Escherichia coli* is preferred in particular from a point of view of introduction and expression efficiency.

The DNA-containing enzyme expression vector of the present invention can be introduced into a host microorganism by a publicly-known method. For example, in cases where *Escherichia coli* is used as a host microorganism, the vector can be introduced into the host cell by using a commercially available *E. coli* HB101 Competent Cell (produced by Takara Bio Inc.).

11. Optically-Active Amine Compounds that can be Synthesized

The following describes optically-active amine compounds that can be synthesized by the present invention and ketone compounds serving as materials for synthesis of the optically-active amine compounds, respectively.

The present invention makes it possible to produce, from a ketone compound represented by general formula (1)

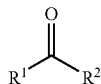
(1)

(where $R^1$ and $R^2$ are each a substitutable alkyl group, a substitutable aralkyl group, or a substitutable aryl group, are allowed to be bonded to each other to form a ring, but are different in structure), a corresponding optically-active amine compound represented by general formula (2)

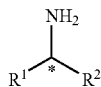
(2)

(where $R^1$ and $R^2$ are as defined in general formula (1) and the mark * indicates an asymmetric carbon atom).

In general formulae (1) and (2), it is preferable that $R^1$ and/or $R^2$ not be a carboxyl group.

For example, the present invention makes it possible to produce, from a ketone compound represented by general formula (3)

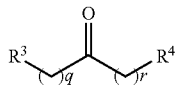
(3)

(where $R^3$ and $R^4$ are each a substitutable C6-C14 aryl group, C4-C14 heteroaryl group, C6-C14 aryloxy group, C4-C14 heteroaryloxy group, C1-C5 alkoxy group, C2-C5 alkoxycarbonyl group, C3-C5 branched-chain alkyl group, C2-C5 alkenyl group, C2-C8 alkynyl group, C5-C7 cycloalkyl group, methyl group, or carboxyl group; q is an integer of 0 to 7, r is an integer of 0 to 2; and q≧r, excluding a case where $R^3$ and $R^4$ are identical and q=r, $R^3$ not being a carboxyl group when q=0, $R^4$ not being a carboxyl group when r=0), an optically-active amine compound represented by general formula (4)

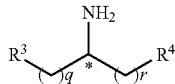
(4)

(where $R^3$, $R^4$, q, and r are as defined in general formula (3) and the mark * indicates an asymmetric carbon atom).

In general formulae (3) and (4), it is preferable that $R^4$ be a methyl group substitutable by a substituent selected from the group consisting of a halogen atom, a nitro group, a hydroxyl group, and a carboxyl group and r be 0 or 1. Examples of the halogen atom include a fluorine atom, a chlorine atom, and a bromine atom. It is more preferable that $R^4$ be a methyl group and r=0.

Further, in general formulae (3) and (4), it is preferable that q be an integer of 0 to 5 and l3 be an aryl group substitutable by a substituent selected from the group consisting of a halogen atom, a nitro group, a hydroxyl group, a cyano group, a C1-C3 alkyl group, a C1-C3 alkoxy group, and a trifluoromethyl group. It is more preferable that q be an integer of 0 to 5 and $R^3$ is a group selected from the group consisting of a methyl group, a methoxy group, an ethoxy group, a phenyl group, a 2-chlorophenyl group, a 3-chlorophenyl group, a 4-chlorophenyl group, a 2-hydroxyphenyl group, a 3-hydroxyphenyl group, a 4-hydroxyphenyl group, a 2-methoxyphenyl group, a 3-methoxyphenyl group, a 4-methoxyphenyl group, a 3,4-dimethoxyphenyl group, a 2-trifluoromethylphenyl group, a 3-trifluoromethylphenyl group, a 4-trifluoromethylphenyl group, a pyridyl group, and a pyrazyl group.

Specific examples of the optically-active amine compound include 1-phenyl-1-aminoethane, 2-amino-3-phenylpropane, 2-amino-3-(3,4-dimethoxyphenyl)propane, 2-amino-3-(4-methoxyphenyl)propane, 2-amino-4-phenylbutane, 2-aminohexane, 2-amino-1-phenyloxypropane, and 2-aminobutanoic acid benzyl ester.

Further, the present invention makes it possible to produce, from a ketone compound represented by general formula (5)

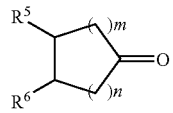
(5)

(where m is an integer of 0 to 2, n is an integer of 2 to 5 (n>m); $R^5$ and $R^6$ are each a halogen atom, a nitro group, a hydroxyl group, a cyano group, an amino group, a carboxyl group, a hydrogen atom, a C6-C14 aryl group, a C4-C14 heteroaryl group, a C6-C14 aryloxy group, a C4-C14 heteroaryloxy group, a C1-C8 alkyl group, a C1-C5 alkoxy group, a C1-C8 alkoxycarbonyl group, a C3-C5 branched-chain alkyl group, a C2-C5 alkenyl group, a C2-C5 alkynyl group, or a C5-C17 cycloalkyl group, each being allowed to have a substituent; and $R^5$ and $R^6$ are allowed to be bonded to each other to form a monocyclic or polycyclic hydrocarbon or a monocyclic or polycyclic heterocycle and are each allowed to have a substituent), an optically-active amine compound represented by general formula (6)

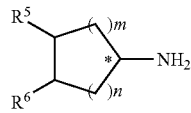
(6)

(where $R^5$, $R^6$, m, and n are as defined in general formula (5) and the mark * indicates an asymmetric carbon atom).

In general formulae (5) and (6), $R^5$ and $R^6$ may be bonded to each other to form a substitutable monocyclic or polycyclic hydrocarbon or a substitutable monocyclic or polycyclic heterocycle. Examples of the monocyclic hydrocarbon include: alicyclic hydrocarbons such as a cyclopropane ring, a cyclobutane ring, a cyclopentane ring, and a cyclohexane ring; and aromatic hydrocarbons such as a benzene ring.

Examples of the polycyclic hydrocarbon include a naphthalene ring and an indene ring. Examples of the monocyclic heterocycle include a furan ring, a thiophene ring, a pyrrole ring, a pyran ring, a pyrrolidine ring, a piperidine ring, and a piperazine ring. Examples of the polycyclic heterocycle include an indole ring, a quinoline ring, and an indoline ring. Examples of the substituent thereof include a halogen atom, a nitro group, a hydroxyl group, a C1-C3 alkyl group, a C1-C3 alkoxy group, and a trifluoromethyl group. Among these, it is preferable that $R^5$ and $R^6$ be bonded to each other to form a substitutable benzene ring. In this case, the substituent is the same as above.

Further, it is preferable that general formulae (5) and (6) each contain a combination of m=1 and n=2, a combination of m=0 and n=3, or a combination m=0 and n=2.

Specific examples of the optically-active amine compound include 1-aminotetraline, 2-aminotetraline, 5-methoxy-2-aminotetraline, 6-methoxy-2-aminotetraline, 7-methoxy-2-aminotetraline, 8-methoxy-2-aminotetraline, and 1-aminoindane.

Further, the present invention makes it possible to synthesize, from a ketone compound represented by general formula (7)

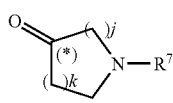

(7)

(where j and k are each an integer of 1 to 3 (k≧4); $R^7$ is a hydrogen atom, a C6-C14 aryl group, a C4-C14 heteroaryl group, a C1-C6 alkyl group, a C1-C6 alkoxy group, a C2-C15 acyl group, a C1-C6 alkoxycarbonyl group, a C7-C15 aralkyl group, a C8-C16 aralkyloxycarbonyl group, or a sulfonyl group substituted by a C1-C6 alkyl group or a C6-C14 aryl group), an optically-active amine compound represented by general formula (8)

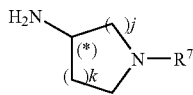

(8)

(where j, k, and $R^7$ are as defined in general formula (7) and the mark * indicates an asymmetric carbon atom).

It is preferable that general formulae (7) and (8) each contain a combination of k=1 and j=1 or a combination of k=2 and j=1.

Further, in general formulae (7) and (8), it is preferable that $R^7$ be a group selected from the group consisting of a hydrogen atom, a phenyl group, a benzyl group, a benzoyl group, a benzyloxycarbonyl group, a t-butyloxycarbonyl group, an ethoxycarbonyl group, a methoxycarbonyl group, a mesyl group, and a tosyl group.

Specific examples of the optically-active amine compound include N-benzyl-3-aminopyrrolidine, N-Boc-3-aminopyrrolidine, N-benzyl-3-aminopiperidine, and N-Boc-3-aminopiperidine.

12. Amination Reaction that Involves the Use of the Enzymes (A) to (C)

In cases where a corresponding optically-active amine compound in which a carbon atom with an amino group bonded thereto serves as an asymmetric point is produced by aminating a ketone compound with use of the enzymes (A) to (C), the production can be performed in, but is not limited to, the following manner.

A ketone compound serving as a substrate, an α-amino acid serving as an amino-group donor for the transaminase (A), a coenzyme that the α-keto acid reductase (B) needs to reduce an α-keto acid, a substrate that the enzyme (C) needs to reduce NAD⁺ to NADH or NADP⁺ to NADPH, and the enzymes (A) to (C) are added to an appropriate solvent such as water or buffer solution and stirred for a reaction under pH control.

The α-amino acid, which serves as an amino-group donor for the transaminase (A), encompasses any α-amino acid that the transaminase (A) can use as an amino-group donor. In particular, α-alanine is preferred for the purpose of obtaining an optically-active amine compound in good yield. It is only necessary to add α-alanine to the reaction system in an equivalent amount of not less than 0.1 with respect to the ketone compound.

The type of coenzyme that the α-keto acid reductase (B) needs to reduce an α-keto acid is determined by the dependence of the α-keto acid reductase (B) on the coenzyme. When the α-keto acid reductase (B) uses NADH as the coenzyme, NADH or NAD⁺ is added. When the α-keto acid reductase (B) uses NADPH as the coenzyme, NADPH or NADP⁺ is added. Further, it is OK to add both types of coenzyme. In the reaction system, a coenzyme is always converted from an oxidized coenzyme into a reduce coenzyme by the coenzyme regenerating ability of the enzyme (C). Therefore, the coenzyme to be added to the reaction system may be a reduced coenzyme or an oxidized coenzyme, and the amount of the coenzyme to be added may be very small. The coenzyme is added to the reaction system in an equivalent amount of not more than 0.01, preferably not more than 0.001, or more preferably not more than 0.0005, with respect to the ketone compound, which serves as a substrate.

Examples of the substrate that the enzyme (C) needs to reduce NAD⁺ to NADH or NADP⁺ to NADPH include glucose in cases where the enzyme (C) is a glucose dehydrogenase, and a formic acid in cases where the enzyme (C) is a formate dehydrogenase. These only need to be added in an equivalent amount of not less than 1.0 with respect to the ketone compound.

The enzymes (A) to (C) to be added to the reaction system may take any form such as purified enzymes, crude enzymes, enzyme-containing substances, microbial culture fluids, products of culture, bacteria, culture fluids, recombinant microorganisms (transformants) having acquired the desired reaction activity through introduction of enzyme genes, products of processing thereof, and commercially available enzymes, provided each has its own desired activity. Among these, a suitably usable example is a transformant able to be obtained by introducing DNA molecules respectively coding for the enzymes (A) to (C) into a host cell and/or a product of culture thereof, examples of which are as follows: three different transformants in which the enzymes (A) to (C) have been expressed respectively and/or products of culture thereof; a transformant in which any two of the enzymes (A) to (C) have been expressed and/or a product of culture thereof and a transformant in which the remaining one of the enzymes (A) to (C) has been expressed and/or a product of culture thereof; and a transformant that expresses the enzymes (A) to (C) in the same bacteria and/or a product of culture thereof. The reason why these transformants are suitably usable is that they make it possible to easily obtain enzymes in large amounts. It is preferable to use the transformant that expresses the enzymes (A) to (C) in the same bacteria and/or a product of culture thereof, because the transformant is faster in speed of conversion from ketone to optically-active amine than the other transformants and high in production of amine per hour.

The amination reaction that involves the use of the enzymes (A) to (C) is performed at a temperature of 5° C. to 80° C., preferably 10° C. to 60° C., or more preferably 20° C. to 40° C. During the reaction, the pH of the reaction liquid is kept at 3 to 10, preferably 4 to 9, or more preferably 5 to 8. The reaction temperature and the reaction pH only need to be timely determined by the enzymes used, the substrates used, and the like.

The reaction is either a batch reaction or a continuous reaction. In the case of a batch reaction, the ketone compound, which serves as a substrate, can be added at an initial concentration of 0.01 to 50% (w/v), preferably 0.1 to 30% (w/v), or more preferably 0.5 to 30% (w/v). Further, the ketone compound may be timely added in process of the reaction.

There is no particular limitation on how to extract the optically-active amine compound from the reaction liquid. However, the optically-active amine compound can be easily obtained with high purity by extracting the optically-active amine compound, either directly from the reaction liquid or after separating bacteria, with a solvent such as ethyl acetate, toluene, t-butylmethylether, hexane, or methylene chloride, and by purifying the optically-active amine compound by distillation or silica gel chromatography after dehydration.

EXAMPLES

The present invention will be further detailed with reference to the following examples. However, the present invention is not limited to these examples. It should be noted that, unless otherwise specified, the following description assumes that "%" means "% by weight".

Example 1

Purification of a Transaminase MTA Derived from *Pseudomonas fluorescens* KNK08-18 (FERM BP-10599), the Cloning of a Structural Gene, and the Building of a Recombinant Vector (pNMTA)

As a microorganism that aminates 1-benzyl-3-pyrrolidinone by using (S)-α-phenethylamine as an amino donor, *Pseudomonas fluorescens* KNK08-18 (FERM BP-10599) was isolated from soil. The microorganism, which is specified by Depository No. FERM DBP-10599, has been deposited at the International Patent Organism Depository of the National Institute of Advanced Industrial Science and Technology (Tsukuba Central 6' 1-1, Higashi 1-chome, Tsukuba-shi, Ibaraki-ken 305-8566 Japan). The purification of a transaminase that catalyzes the reaction, the cloning of a structural gene thereof, and the building of a recombinant vector containing the structural gene were performed. It should be noted that the present enzyme is hereinafter referred to as "MTA". The MTA is an example of the "transaminase (A)" of the present invention.

(How to Measure Activity in a Purification Step)

To 0.9 ml of substrate solution made up in the following way, 0.1 mL of purified enzyme solution were added. The solutions were allowed to react with each other at 30° C. for one hour. The reaction was stopped by adding 0.1 ml of 3 N hydrochloric acid. Thus produced was 1-benzyl-3-aminopyrrolidine, which was then quantified by high-performance liquid chromatography. The value thus obtained was used to calculate an activity value.

[Composition of the Substrate Solution]

| | |
|---|---|
| (S)-α-phenethylamine | 28.3 mM |
| 1-benzyl-3-pyrrolidinone | 28.3 mM |
| Pyridoxal phosphate | 0.02 mM |
| Calcium phosphate buffer solution (with a pH of 7.0) | 0.1 M |

[Conditions for Measurement by High-Performance Liquid Chromatography]

Column: Finepak SIL C18-T (manufactured by JASCO Corporation)

Eluant: distilled water 1260 mL/acetonitrile 740 mL/$KH_2PO_4$ 10 g/SDS 2.88 g (with a pH of 3.6)

Flow rate: 1 ml/min.

Detection: 254 nm

Column temperature: 40° C.

(Extraction and Purification of the Transaminase MTA)

*Pseudomonas fluorescens* KNK08-18 (FERM BP-10599) was inoculated into 50 mL of an S17 culture medium (Composition: 5 g/L $KH_2PO_4$, 5 g/L $K_2HPO_4$, 0.16 g/L $MgSO_4.7H_2O$, 0.018 g/L $FeSO_4.7H_2O$, 0.012 g/L $ZnSO_4.H_2O$, 0.002 g/L $MnSO_4.7H_2O$, 0.001 g/L $CuSO_4.7H_2O$, 0.02 g/L NaCl, 20 g/L glycerin, 10 g/L yeast extract (produced by Nihon Pharmaceutical Co., Ltd.), 500 mg/L (S)-7-methoxy-2-aminotetraline (with a pH of 7.2)) in a 500 mL Sakaguchi flask, and was then cultured at 30° C. for a day. Thus obtained was a preculture fluid. Next, the preculture fluid thus obtained was inoculated into 0.3 L of a culture medium (made up in the same way as above) in a 5 L mini-jar, and was then cultured at 30° C. for 28 hours with a ventilation volume of 0.6 vvm and an agitation speed of 400 rpm. Then, bacteria were collected from the culture fluid by centrifugation, and were then suspended in 0.01 M calcium phosphate buffer solution (with a pH of 8.0) containing 0.01% 2-mercaptoethanol and 0.02 mM pyridoxal phosphate. The suspension thus obtained was grounded by ultrasonic grinding. Next, a cell-free extract was prepared by removing a solid from the ground product by centrifugation.

Removal of nucleic acid was performed through addition of protamine sulfate to the cell-free extract thus obtained. Ammonium sulfate was added to the resultant protamine sulfate-treated liquid so that saturation was 30%, and was then dissolved. After that, the sediment thus produced was removed by centrifugation. Ammonium sulfate was added to the supernatant so that saturation was 60%, and was then dissolved. After that, the sediment produced by centrifugation was collected.

The sediment was dissolved in 10 mM phosphate buffer solution (with a pH of 0.8) containing 0.01% 2-mercaptoethanol, 20 mM pyridoxal phosphate, and 0.1 mM phenylmethylsulfonyl fluoride (PMSF), and the resultant solution was dialyzed with the same buffer solution. The resultant product was supplied to a DEAE-TOYOPEARL 650M column (300 mL; manufactured by Tosoh Corporation) equilibrated with the same buffer solution, and an active fraction was absorbed. After the column was washed with the same buffer solution, the active fraction was eluted by a linear gradient (from 0 M to 0.3 M) of sodium chloride.

The active fraction thus eluted was collected, and ammonium sulfate was dissolved in the active fraction so that final concentration was 1.2 M. The resultant product was supplied to a Phenyl-TOYOPEARL 650M column (120 mL; manufactured by Tosoh Corporation) equilibrated in advance with 10 mM phosphate buffer solution (with a pH of 0.8) containing 1.2 M ammonium sulfate, 0.01% 2-mercaptoethanol, 20 mM pyridoxal phosphate, and 0.1 mM PMSF, and an active fraction was absorbed. After the column was washed with the same buffer solution, the active fraction was eluted by a linear gradient (from 1.2 M to 0 M) of ammonium sulfate. The active fraction was collected, and was then dialyzed with 10 mM phosphate buffer solution (pH 0.8) containing 0.01% 2-mercaptoethanol, 20 mM pyridoxal phosphate, and 0.1 mM PMSF was dialyzed.

The crude enzyme solution thus obtained was supplied to a Q-sepharose 16/10 HP column (manufactured by Amersham Biosciences) equilibrated in advance with 10 mM phosphate buffer solution (pH 0.8) containing 0.01% 2-mercaptoethanol, 20 mM pyridoxal phosphate, and 0.1 mM PMSF, and an active fraction was absorbed. After the column was washed with the same buffer solution, the active fraction was eluted by a linear gradient (from 0 M to 0.7 M) of sodium chloride.

The active fraction thus eluted was collected, and ammonium sulfate was dissolved in the active fraction so that final concentration was 1.0 M. The resultant product was supplied to a Butyl-TOYOPEARL 650S column (25 mL; manufactured by Tosoh Corporation) equilibrated in advance with 10 mM phosphate buffer solution (with a pH of 0.8) containing 1.0 M ammonium sulfate, 0.01% 2-mercaptoethanol, 20 mM pyridoxal phosphate, and 0.1 mM PMSF, and an active fraction was absorbed. After the column was washed with the same buffer solution, the active fraction was eluted by a linear gradient (from 1.0 M to 0 M) of ammonium sulfate. The active crude enzyme solution thus obtained was condensed by ultrafiltration.

The crude enzyme liquid thus condensed was supplied to a HiLoad 16/60 Superdex 200 p/g column (manufactured by Amersham Biosciences) equilibrated in advance with 10 mM phosphate buffer solution (with a pH of 0.8) containing 0.01% 2-mercaptoethanol, 20 mM pyridoxal phosphate, 0.1 mM PMSF, and 0.15 M sodium chloride. Thus obtained was an electrophoretically-uniform purified enzyme preparation.

(Base Sequence Determination of the MTA Structural Gene)

An N terminal amino-acid sequence of the purified MTA thus obtained was determined by a Protein Sequencer ABI492 (manufactured by Applied Biosystems). Further, the purified MTA thus obtained was denatured in the presence of 8 M urea, and was then digested with an achromobacter-derived lysyl endopeptidase (manufactured by Wako Pure Chemical Industries, Ltd.). Thus obtained was a peptide fragment. An amino-acid sequence of the peptide fragment thus obtained was determined in the same manner as the N terminal amino-acid sequence. In consideration of a base sequence expected from this amino-acid sequence, Primer 1 (SEQ ID NO: 3 of the Sequence Listing) and Primer 2 (SEQ ID NO: 4 of the Sequence Listing), each of which serves to amplify a part of the MTA gene through a PCR, were synthesized.

Chromosome DNA was extracted from the culture fluid of Pseudomonas fluorescens KNK08-18 (FERM BP-10599) according to a method taught by Murray et al. (*Nucl. Acids Res.*, 8, 4321, 1980). Primers 1 and 2 thus synthesized were used to perform a PCR for which the chromosome DNA thus obtained served as a template. Thus obtained was a DNA fragment of approximately 540 bp considered to be a part of the MTA gene. The PCR was performed by using a TaKaRa Ex Taq (produced by Takara Bio Inc.), and the reaction conditions were in conformity with an instruction manual therefor.

The DNA fragment was cloned in a plasmid pT7Blue T-Vector (produced by Novagen), and a base sequence thereof was determined with use of a Dye Terminator Cycle Sequencing Ready Reaction Kit ABI PRISM (manufactured by Applied Biosystems) and a DNA Sequencer ABI 310 (manufactured by Applied Biosystems).

The chromosome DNA of *Pseudomonas fluorescens* KNK08-18 was completely digested with a restriction enzyme EcoRI, FbaI, NcoI, or SphI, and each of the digested products thus obtained was intramolecularly cyclized with use of a T4DNA ligase (produced by Takara Bio Inc.). With use of the resultant product as a template, the entire base sequence of the MTA gene on the chromosome DNA was determined by an inverse PCR method (*Nucl. Acids Res.*, 16, 8186 (1988)) on the basis of the above-identified partial base sequence information on the MTA gene. The PCR was performed by using a TaKaRa LA Taq with GC buffer (produced by Takara Bio Inc.), and the reaction conditions were in conformity with an instruction manual therefor. The base sequence thus determined is represented by SEQ ID NO: 5 of the Sequence Listing. Further, an amino-acid sequence coded for by the base sequence is represented by SEQ ID NO: 6 of the Sequence Listing.

(Preparation of a Recombinant Vector Containing the MTA Structural Gene)

Based on the base sequence thus determined, Primer 3 (SEQ ID NO: 7 of the Sequence Listing) and Primer 4 (SEQ ID NO: 8 of the Sequence Listing) were synthesized by adding an NdeI cleavage site to a start codon of the MTA structural gene and by adding an EcoRI cleavage site immediately after a stop codon of the MTA structural gene, respectively. With use of the already-obtained chromosome DNA of the *Pseudomonas fluorescens* KNK08-18 as a template, these primers were used to perform a PCR through which duplex DNA was obtained by adding the NdeI cleavage site to the start codon of the MTA structural gene and by adding the EcoRI cleavage site immediately after the stop codon of the MTA structural gene. The PCR was performed by using a TaKaRa LA Taq with GC buffer (produced by Takara Bio Inc.), and the reaction conditions were in conformity with an instruction manual therefor. The DNA was digested with NdeI and EcoRI, and was then inserted between an NdeI cleavage site and an EcoRI cleavage site downstream of a lac promoter of a plasmid pUCN18 (a plasmid in which an NdeI cleavage site had been destructed by altering the 185th T of pUC18 (produced by Takara Bio Inc., GenBank Accession No. L09136) to A by a PCR method and into which a new NdeI cleavage site had been introduced by further altering the 471st and 472nd GC to TG). Thus obtained was a recombinant vector pNMTA. FIG. 1 shows a simple illustration of the procedure for building the recombinant vector pNMTA.

Example 2

Cloning of a Structural Gene of a Transaminase TPS Derived from *Pseudomonas* sp. KNK425 (FERM BP-6525) and the Building of a Recombinant Vector (pNTPS)

A structural gene of an (S)-α-phenethylamine: pyruvic transaminase, i.e., a transaminase derived from *Pseudomonas* sp. KNK425 (FERM BP-6525), which is described in International Publication No. WO 00/26351 Pamphlet, was cloned. Furthermore, a recombinant vector containing the present structural gene was built. It should be noted here that the present enzyme will be hereinafter referred to as "TPS".

The TPS is an example of the "transaminase (A)" of the present invention. The microorganism, which is specified by Depository No. FERM BP-6525, has been deposited at the International Patent Organism Depository of the National Institute of Advanced Industrial Science and Technology (Tsukuba Central 6, 1-1, Higashi 1-chome, Tsukuba-shi, Ibaraki-ken 305-8566 Japan).

(Base Sequence Determination of the TPS Structural Gene)

SEQ ID NO: 1 of International Publication No. WO 00/26351 Pamphlet describes an N terminal amino-acid sequence of TPS. On the basis of the N terminal amino-acid sequence, Primer 5 (SEQ ID NO: 9 of the Sequence Listing) and Primer 6 (SEQ ID NO: 10 of the Sequence Listing) were synthesized for use in an inverse PCR.

Chromosome DNA was extracted from the culture fluid of *Pseudomonas* sp. KNK425 according to a method taught by Murray et al. (*Nucl. Acids Res.*, 8, 4321, 1980). The chromosome DNA was completely digested with a restriction enzyme AatI, ApaI, BamHI, SacI, SaiI, SphI, XhoI, or NspV, and each of the digested products thus obtained was intramolecularly cyclized with use of a T4DNA ligase (produced by Takara Bio Inc.). With use of the resultant product as a template, Primers 5 and 6 were used to perform a PCR by which a partial base sequence of the TPS structural gene on the chromosome DNA was determined. The PCR was performed by using a TaKaRa LA Taq with GC buffer (produced by Takara Bio Inc.), and the reaction conditions were in conformity with an instruction manual therefor. The base sequence was deciphered with use of a Dye Terminator Cycle Sequencing Ready Reaction Kit ABI PRISM (manufactured by Applied Biosystems) and a DNA Sequencer ABI 310 (manufactured by Applied Biosystems).

Furthermore, the chromosome DNA thus prepared was completely digested with a restriction enzyme ApaI, SalI, XhoI, or NspV, and each of the digested products thus obtained was intramolecularly cyclized with use of a T4DNA ligase (produced by Takara Bio Inc.). With use of the cyclized DNA as a template, the entire base sequence of the TPS gene on the chromosome DNA was determined by an inverse PCR method on the basis of the above-identified partial base sequence information on the TPS gene. The PCR were performed in the same manner as above, and the base sequence was determined in the same manner as above. The base sequence thus determined is represented by SEQ ID NO: 2 of the Sequence Listing. Further, an amino-acid sequence coded for by the base sequence is represented by SEQ ID NO: 1 of the Sequence Listing.

(Preparation of a Recombinant Vector Containing the TPS Structural Gene)

Based on the base sequence thus determined, Primer 7 (SEQ ID NO: 11 of the Sequence Listing) and Primer 8 (SEQ ID NO: 12 of the Sequence Listing) were synthesized by adding an NdeI cleavage site to a start codon of the TPS structural gene and by adding a stop codon TAA and an SacI cleavage site immediately after a stop codon of the TPS structural gene, respectively. With use of the already-obtained chromosome DNA of *Pseudomonas* sp. KNK425 as a template, these primers were used to perform a PCR through which duplex DNA was obtained by adding the NdeI cleavage site to the start codon of the TPS structural gene and by adding the EcoRI cleavage site immediately after the stop codon of the TPS structural gene. The PCR was performed by using a Pyrobest DNA Polymerase (produced by Takara Bio Inc.), and the reaction conditions were in conformity with an instruction manual therefor. The DNA was digested with NdeI and SacI, and was then inserted between an NdeI cleavage site and an SacI cleavage site downstream of a lac promoter of a plasmid pUCN18 (a plasmid in which an NdeI cleavage site had been destructed by altering the 185th T of pUC18 (produced by Takara Bio Inc., GenBank Accession No. L09136) to A by a PCR method and into which a new NdeI cleavage site had been introduced by further altering the 471st and 472nd GC to TG). Thus obtained was a recombinant vector pNTPS. FIG. 1 shows a simple illustration of the procedure for building the recombinant vector pNTPS.

Example 3

Cloning of a Structural Gene of a Transaminase TAS Derived from *Arthrobacter* sp. KNK168 (FERM BP-5228) and the Building of a Recombinant Vector (pNTAS)

In order to efficiently express a polypeptide having aminotransferase activity and coded for by DNA of a base sequence represented by SEQ ID NO: 2 of International Publication No. WO 98/48030 Pamphlet, a recombinant vector was newly built. It should be noted that the polypeptide having aminotransferase activity will be hereinafter referred to as "TAS". The TAS is an example of the "transaminase (A)" of the present invention. The microorganism, which is specified by Depository No. FERM BP-5228, has been deposited at the International Patent Organism Depository of the National Institute of Advanced Industrial Science and Technology (Tsukuba Central 6, 1-1, Higashi 1-chome, Tsukuba-shi, Ibaraki-ken 305-8566 Japan).

(Preparation of a Recombinant Vector Containing the TAS Structural Gene)

Based on the base sequence represented by SEQ ID NO: 2 of International Publication No. WO 98/48030 Pamphlet, Primer 9 (SEQ ID NO: 13 of the Sequence Listing) was synthesized by adding an NdeI cleavage site to a start codon of the TAS structural gene, and Primer 10 (SEQ ID NO: 14) was synthesized by adding a stop codon TAA and an SacI cleavage site immediately after a stop codon of the TAS structural gene and destructing the SacI site through introduction of a silent mutation into a base triplet. With use of a plasmid pAT28, obtained by a method described in International Publication No. WO 98/48030 Pamphlet, as a template, these primers were used to perform a PCR through which duplex DNA was obtained by adding the NdeI cleavage site to the start codon of the TAS structural gene and by adding the stop codon TAA and the SacI cleavage site immediately after the stop codon and introducing the silent mutation into the base triplet. The PCR was performed by using a Pyrobest DNA Polymerase (produced by Takara Bio Inc.), and the reaction conditions were in conformity with an instruction manual therefor. The DNA was digested with NdeI and SacI, and was then inserted between an NdeI cleavage site and an SacI cleavage site downstream of a lac promoter of a plasmid pUCN18 (a plasmid in which an NdeI cleavage site had been destructed by altering the 185th T of pUC18 (produced by Takara Bio Inc., GenBank Accession No. L09136) to A by a PCR method and into which a new NdeI cleavage site had been introduced by further altering the 471st and 472nd GC to TG). Thus obtained was a recombinant vector pNTAS. FIG. 1 shows a simple illustration of the procedure for building the recombinant vector pNTAS. A base sequence of the TAS structural gene introduced into the vector pNTAS is represented by SEQ ID NO: 25 of the Sequence Listing. Further, an amino-acid sequence coded for by the base sequence, i.e., an amino-acid sequence of TAS is represented by SEQ ID NO: 26 of the Sequence Listing.

Example 4

Building of Three Types of Recombinant

Vector (pNPAG, pUCPAG, and pSTVPAG) Containing Both of the Genes, a Structural Gene of an L-lactate Dehydrogenase PALDH Derived from *Pediococcus acidilactici* Strain JCM8797, and a Structural Gene of a Glucose Dehydrogenase GDH Derived from *Bacillus megaterium* Strain IAM1030

(4-1. Building of an Expression Vector (pNG) Containing a Glucose Hydrogenase Gene)

Primer 11 (SEQ ID NO: 15 of the Sequence Listing) and Primer 12 (SEQ ID NO: 16 of the Sequence Listing) were used to perform a PCR by using a vector pGDKI (*Eur. J. Biochem.*, 186, 389 (1989)) as a template. Thus obtained was duplex DNA in which a ribosome binding sequence of *Escherichia coli* had been added five bases upstream of a start codon of a glucose dehydrogenase (hereinafter referred to as "GDH") derived from *Bacillus megaterium* strain IAM1030, an EcoRI cleavage site had been added immediately before the ribosome binding sequence of *Escherichia coli*, and an SalI cleavage site had been added immediately after a stop codon. The GDH is an example of the "enzyme (C)" of the present invention.

The DNA fragment thus obtained was digested with EcoRI and SalI, and was then inserted between an EcoRI cleavage site and an SalI cleavage site downstream of a lac promoter of a plasmid pUCN18 (a plasmid in which an NdeI cleavage site had been destructed by altering the 185th T of pUC18 (produced by Takara Bio Inc., GenBank Accession No. L09136) to A by a PCR method and into which a new NdeI cleavage site had been introduced by further altering the 471st and 472nd GC to TG). Thus built was a recombinant vector pNG.

(4-2. Cloning of an L-lactate Dehydrogenase from *Pediococcus acidilactici* Strain JCM8797)

A gene of an L-lactate dehydrogenase (hereinafter abbreviated as "PALDH"), which is a type of α-keto reductase, was cloned from *Pediococcus acidilactici* strain JCM8797 in the following manner. *Pediococcus acidilactici* strain JCM8797 is available from the RIKEN BioResource Center (3-1-1 Takanodai, Tsukuba-shi, Ibaraki-ken 305-0074 Japan) to a person skilled in the art. The PALDH is an example of the "α-keto acid reductase (B)" of the present invention.

Based on estimated amino-acid sequence information on a known L-lactate dehydrogenase registered in a gene data bank, Primer 13 (SEQ ID NO: 17 of the Sequence Listing) and Primer 14 (SEQ ID NO: 18 of the Sequence Listing), each of which serves to amplify through a PCR a part of the gene that codes for PALDH, were synthesized.

Chromosome DNA of *Pediococcus acidilactici* strain JCM8797 was prepared with use of a commercially available UltraClean Microbiol DNA Isolation Kit (manufactured by MO BIO Laboratories, Inc) in conformity with an instruction manual therefor. DNA Primers 13 and 14 thus prepared were used to perform a PCR for which the chromosome DNA thus obtained served as a template. Thus amplified was a DNA fragment of approximately 0.3 kbp considered to be a part of the target gene. The PCR was performed by using a TaKaRa Ex Taq (produced by Takara Bio Inc.) as a DNA polymerase, and the reaction conditions were in conformity with an instruction manual therefor. The DNA fragment was cloned in a plasmid pT7Blue T-Vector (produced by Novagen), and a base sequence thereof was analyzed with use of a BigDye Terminator Sequencing Standard Kit (manufactured by Applied Biosystems) and a Genetic Analyzer ABI PRISM 3100 (manufactured by Applied Biosystems).

The chromosome DNA thus prepared of *Pediococcus acidilactici* strain JCM8797 was completely digested with a restriction enzyme FbaI, and the resultant mixture of DNA fragments thus obtained was intramolecularly cyclized with use of a T4 ligase. With use of the resultant product as a template, the entire base sequence of the PALDH structural gene was determined by an inverse PCR method (*Nucl. Acids Res.*, 16, 8186 (1988)). The result is represented by SEQ ID NO: 19 of the Sequence Listing. The inverse PCR was performed by using a TaKaRa Ex Taq (produced by Takara Bio Inc.) as a DNA polymerase, and the reaction conditions were in conformity with an instruction manual therefor. Further, an amino-acid sequence coded for by the base sequence represented by SEQ ID NO: 19 is represented by SEQ ID NO: 20.

(4-3. Building of an Expression Vector pNPAG Containing the PALDH Structural Gene and the GDH Structural Gene)

Primer 15 (SEQ ID NO: 21 of the Sequence Listing) and Primer 16 (SEQ ID NO: 22 of the Sequence Listing) were used to perform a PCR for which the chromosome DNA thus obtained of *Pediococcus acidilactici* strain JCM8797 served as a template. Thus obtained was duplex DNA in which an NdeI cleavage site had been added to a start codon of a gene consisting of the base sequence represented by SEQ ID NO: 19 and a stop codon TAA and an EcoRI cleavage site had been added immediately after a stop codon. The PCR was performed by using a TaKaRa Ex Taq (produced by Takara Bio Inc.) as a DNA polymerase, and the reaction conditions were in conformity with an instruction manual therefor. The DNA was partially digested with NdeI and EcoRI, and was then inserted between an NdeI cleavage site and an EcoRI cleavage site of the already-prepared recombinant vector pNG. Thus built was a recombinant vector pNPAG.

(4-4. Expression Vectors pUCPAG and pSTVPAG Each Containing the PALDH Structural Gene and the GDH Structural Gene)

Primer 17 (SEQ ID NO: 23 of the Sequence Listing) and Primer 18 (SEQ ID NO: 24 of the Sequence Listing) were used to perform a PCR for which the recombinant vector thus prepared served as a template. Thus obtained was duplex DNA in which a ribosome binding sequence of *Escherichia coli* had been added five bases upstream of a start codon of the PALDH structural gene, an SacI cleavage site had been added immediately before the ribosome binding sequence of *Escherichia coli*, a stop codon TAA and an SphI cleavage site had been added immediately after a stop codon of the GDH structural gene, and the PALDH structural gene and the GDH structural gene had been bonded together. The duplex DNA was digested with SacI and SphI, and was then inserted between an SacI cleavage site and an SphI cleavage site of a plasmid pUC19 (produced by Takara Bio Inc.). Thus built was a recombinant vector pUCPAG. Furthermore, a recombinant vector pSTVPAG was built through the same processing by using a plasmid pSTV28 (produced by Takara Bio Inc.) instead of using the plasmid pUC19.

Figure 2:
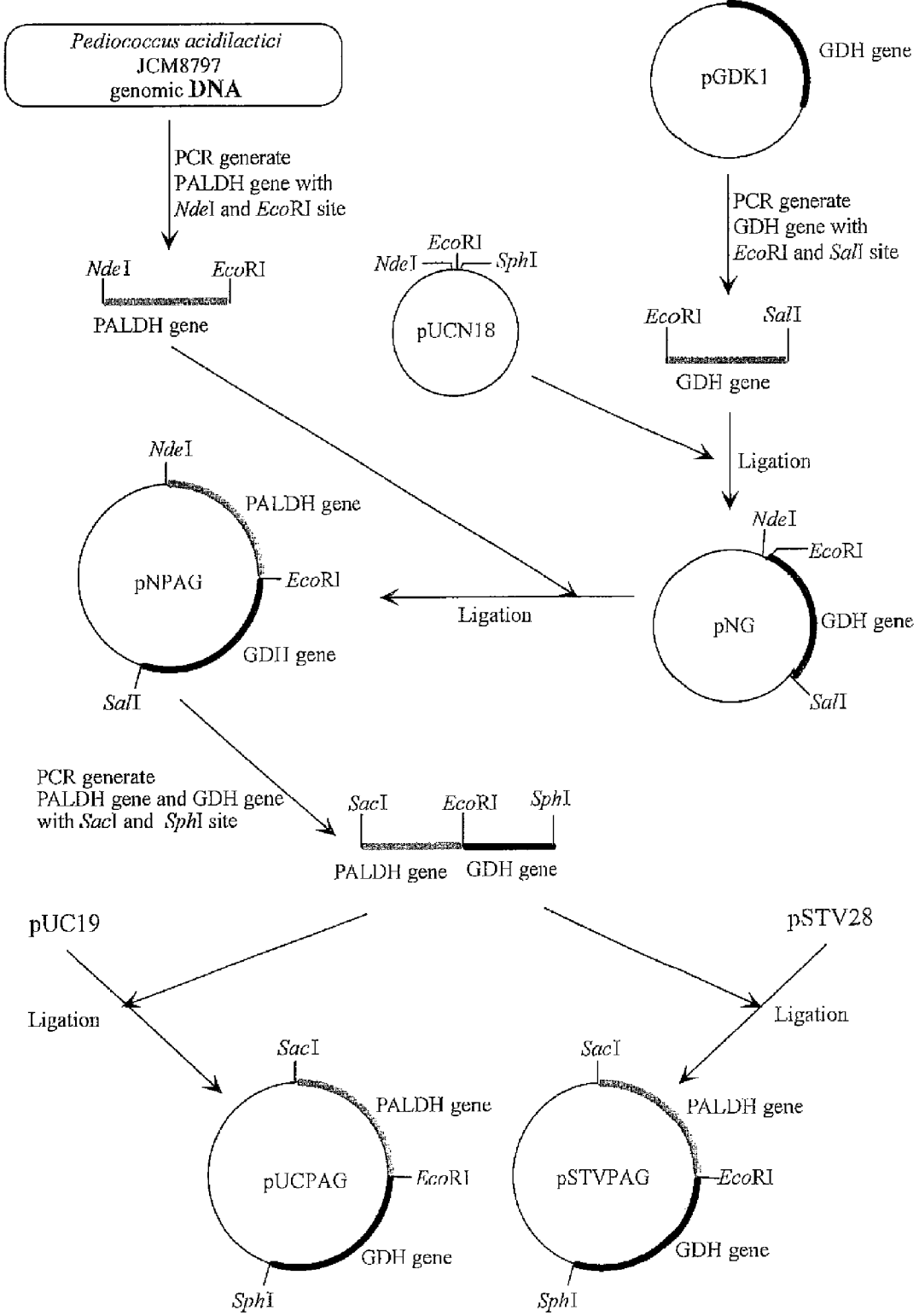
FIG. 2 is a schematic diagram of respective procedures for building recombinant plasmids pNG, pNPAG, pUCPAG, and pSTVPAG.

FIG. 2 shows a simple illustration of the procedures for building the recombinant plasmids pNG, pNTPAG, pUCPAG, and pSTVPAG.

Example 5

Figure 3:
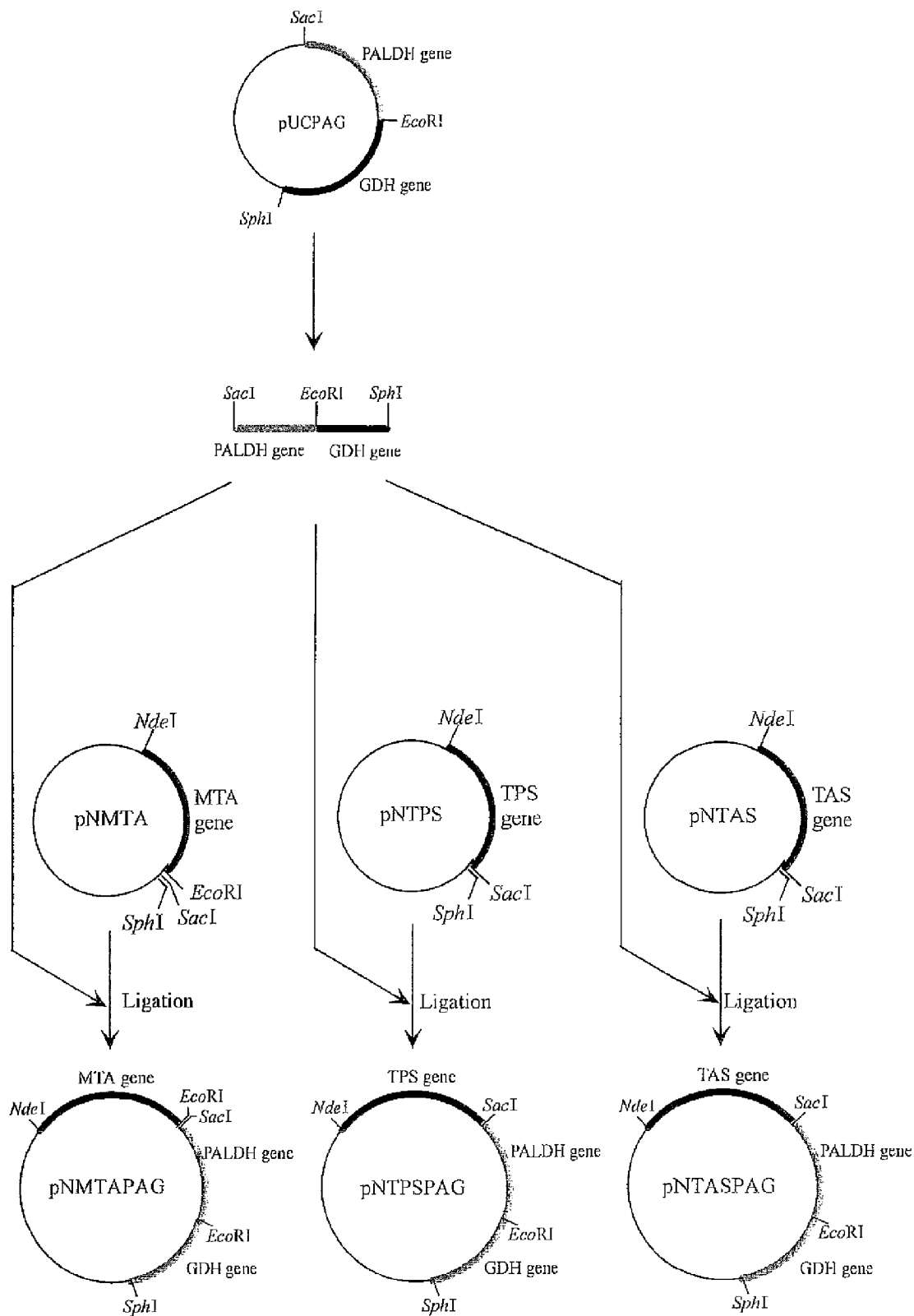
FIG. 3 is a schematic diagram of respective procedures for building recombinant plasmids pNMTAPAG, pNTPSPAG, and pNTASPAG.

Building of a Recombinant Vector (pNMTAPAG) Containing the Three Structural Genes MTA, PALDH, and GDH Duplex DNA, obtained by digesting the pUCPAG of Example 4 with SacI and SphI, in which the PALDH structural gene and the GDH structural gene had been bonded together was inserted between an SacI cleavage site and an SphI cleavage site of the recombinant vector pNMTA obtained in Example 1. Thus obtained was a recombinant vector pNMTAPAG. FIG. 3 shows a simple illustration of the procedure for building the recombinant vector pNMTAPAG.

Example 6

Building of a Recombinant Vector (pNTPSPAG) Containing the Three Structural Genes TPS, PALDH, and GDH Duplex DNA, obtained by digesting the pUCPAG of Example 4 with SacI and SphI, in which the PALDH structural gene and the GDH structural gene had been bonded together was inserted between an SacI cleavage site and an SphI cleavage site of the recombinant vector pNTPS obtained in Example 2. Thus obtained was a recombinant vector pNTPSPAG. FIG. 3 shows a simple illustration of the procedure for building the recombinant vector pNTPSPAG.

Example 7

Building of a Recombinant Vector (pNTASPAG) Containing the Three Structural Genes TAS, PALDH, and GDH Duplex DNA, obtained by digesting the pUCPAG of Example 4 with SacI and SphI, in which the PALDH structural gene and the GDH structural gene had been bonded together was inserted between an SacI cleavage site and an SphI cleavage site of the recombinant vector pNTAS obtained in Example 3. Thus obtained was a recombinant vector pNTASPAG. FIG. 3 shows a simple illustration of the procedure for building the recombinant vector pNTASPAG.

Example 8

Breeding of Recombinant *Escherichia coli* that Expresses MTA, PALDH, and GDH (1)

Recombinant *E. coli* HB101 (pNMTAPAG) was obtained by transforming *E. coli* HB101 (produced by Takara Bio Inc.) with use of the recombinant plasmid pNMTAPAG prepared in Example 5. As a comparative example, recombinant *E. coli* HB101 (pUCN18) was obtained by transforming *E. coli* HB101 (produced by Takara Bio Inc.) with use of the plasmid pUCN18.

Each of the recombinant *E. coli* HB101 (pNMTAPAG) and the recombinant *E. coli* HB101 (pUCN18), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 32° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. Specific activity was calculated by measuring the MAT activity, PALDH activity, and GDH activity of the cell-free extract in the following manners, respectively. It should be noted that the concentration of protein in the cell-free extract was measured with use of a protein assay kit (manufactured Bio-Rad Laboratories).

(How to Measure MTA Activity)

To 0.8 ml of a substrate solution made up in the following way, 0.2 ml of enzyme solution were added. The solutions were allowed to react with each other at 30° C. for one hour. The reaction was stopped by adding 50 μl of 6 N hydrochloric acid. Thus produced was acetophenone, which was then quantified by high-performance liquid chromatography. Under the present reaction conditions, the activity with which 1 μmol of acetophenone had been produced per minute was defined as 1 U.

[Composition of the Substrate Solution]

| | |
|---|---|
| (S)-α-phenethylamine | 25 mM |
| Pyruvic acid | 25 mM |
| Pyridoxal phosphate | 0.063% |
| Tris-HCl buffer solution (with a pH of 8.0) | 0.1 M |

[Conditions for Measurement by High-Performance Liquid Chromatography]

Column: YMC-Pack C18 A303 (manufactured by YMC Co., Ltd.)
Eluant: distilled water 700 mL/acetonitrile 300 mL/$KH_2PO_4$ 3.05 g/phosphoric acid 1.25 g
Flow rate: 1 ml/min.
Detection: 210 nm
Column temperature: room temperature (How to Measure PALDH Activity)

The PALDH activity was calculated from the rate of diminution in absorbance at 340 nm of a reaction liquid, obtained by dissolving a pyruvic acid and a coenzyme NADH in 100 mM phosphate buffer solution (with a pH of 6.5) so that the pyruvic acid had a final concentration of 30 mM and the coenzyme NADH had a final concentration of 0.25 mM and by further adding an enzyme solution, which had reacted at 30° C. for one minute. Under the present reaction conditions, the activity with which 1 μmol of NADH had been oxidized to $NAD^+$ per minute was defined as 1 U.

(How to Measure GDH Activity)

The GDH activity was calculated from the rate of increase in absorbance at 340 nm of a reaction liquid, obtained by dissolving glucose and a coenzyme $NADP^+$ in 1 M Tris-HCl buffer solution (with a pH of 8) so that the glucose had a final concentration of 0.1 M and the coenzyme $NADP^+$ had a final concentration of 2 mM and by further adding an enzyme solution, which had reacted at 25° C. for one minute. Under the present reaction conditions, the activity with which 1 μmol of $NADP^+$ had been reduced to NADPH per minute was defined as 1 U.

The specific activity of each of MTA, PALDH, and GDH of *E. coli* HB101 (pUCN18), which serves as a comparative example, was not more than 0.1 U/mg. As such, *E. coli* HB101 (pUCN18) exhibited virtually no activity of any one of the three enzymes. On the other hand, *E. coli* HB101 (pNMTAPAG) was found to have expressed all the three enzymes. As such, *E. coli* HB101 (pNMTAPAG) exhibited an MTA specific activity of 55 U/mg, a PALDH specific activity of 713 U/mg, and a GDH specific activity of 153 U/mg.

Example 9

Breeding of Recombinant *Escherichia coli* that Expresses MTA, PALDH, and GDH (2)

Recombinant *E. coli* HB101 (pNMTA, pSTVPAG) was obtained by transforming *E. coli* HB101 (produced by Takara Bio Inc.) with use of the recombinant vector pNMTA, prepared in Example 1, which serves to express MTA and the recombinant vector pSTVPAG, prepared in Example 4, which serves to express PALDH and GDH. As a comparative example, recombinant E. coli HB101 (pUCN18, pSTV28) was obtained by transforming E. coli HB101 (produced by Takara Bio Inc.) with use of the plasmids pUCN18 and pSTV28 (produced by Takara Bio Inc.).

Each of the recombinant E. coli HB101 (pNMTA, pSTVPAG) and the recombinant E. coli HB101 (pUCN18, pSTV28), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin and 50 μg/ml of chloramphenicol, and was then cultured with shaking at 32° C. for 24 hours. A cell-free extract was prepared in the same manner as in Example 8, and then the specific activity of each enzyme was measured in the same manner as in Example 8.

The specific activity of each of MTA, PALDH, and GDH of E. coli HB101 (pUCN18, pSTV28), which serves as a comparative example, was not more than 0.1 U/mg. As such, E. coli HB101 (pUCN18, pSTV28) exhibited virtually no activity of any one of the three enzymes. On the other hand, E. coli HB101 (pNMTA, pSTVPAG) was found to have expressed all the three enzymes. As such, E. coli HB101 (pNMTA, pSTVPAG) exhibited an MTA specific activity of 15.7 U/mg, a PALDH specific activity of 82 U/mg, and a GDH specific activity of 9 U/mg.

Example 10

Breeding of Recombinant *Escherichia coli* that Expresses TPS, PALDH, and GDH

Recombinant E. coli HB101 (pNTPSPAG) was obtained by transforming E. coli HB101 (produced by Takara Bio Inc.) with use of the recombinant plasmid pNTPSPAG prepared in Example 6. As a comparative example, recombinant E. coli HB101 (pUCN18) was obtained by transforming E. coli HB101 (produced by Takara Bio Inc.) with use of the plasmid pUCN18.

Each of the recombinant E. coli HB101 (pNTPSPAG) and the recombinant E. coli HB101 (pUCN18), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 32° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. Specific activity was calculated by measuring each of the TPS activity, PALDH activity, and GDH activity of the cell-free extract. It should be noted that the PALDH activity, the GDH activity, and the concentration of protein in the cell-free extract were measured in the same manners as in Example 8. Further, the TPS activity was measured in the same manner as the MAT activity was measured in Example 8.

The specific activity of each of TPS, PALDH, and GDH of E. coli HB10 (pUCN18), which serves as a comparative example, was not more than 0.1 U/mg. As such, E. coli HB101 (pUCN18) exhibited virtually no activity of any one of the three enzymes. On the other hand, E. coli HB101 (pNTPSPAG) was found to have expressed all the three enzymes. As such, E. coli HB101 (pNTPSPAG) exhibited a TPS specific activity of 11 U/mg, a PALDH specific activity of 323 U/mg, and a GDH specific activity of 113 U/mg.

Example 11

Breeding of Recombinant *Escherichia coli* that Expresses TAS, PALDH, and GDH

Recombinant E. coli HB101 (pNTASPAG) was obtained by transforming E. coli HB101 (produced by Takara Bio Inc.) with use of the recombinant plasmid pNTASPAG prepared in Example 7. As a comparative example, recombinant E. coli HB101 (pUCN18) was obtained by transforming E. coli HB101 (produced by Takara Bio Inc.) with use of the plasmid pUCN18.

Each of the recombinant E. coli HB101 (pNTASPAG) and the recombinant E. coli HB101 (pUCN18), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 32° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. Specific activity was calculated by measuring each of the TAS activity, PALDH activity, and GDH activity of the cell-free extract. It should be noted that the PALDH activity, the GDH activity, and the concentration of protein in the cell-free extract were measured in the same manners as in Example 8. Further, the TAS activity was measured in the following manner.

(How to Measure TAS Activity)

To 0.8 ml of a substrate solution made up in the following way, 0.2 ml of enzyme solution were added. The solutions were allowed to react with each other at 30° C. for one hour. The reaction was stopped by adding 50 μl of 6 N hydrochloric acid. Thus produced was acetophenone, which was then quantified by the high-performance liquid chromatography described in Example 8. Under the present reaction conditions, the activity with which 1 μmol of acetophenone had been produced per minute was defined as 1 U.

[Composition of the Substrate Solution]

| | |
|---|---|
| (R)-α-phenethylamine | 25 mM |
| Pyruvic acid | 25 mM |
| Pyridoxal phosphate | 0.063% |
| Tris-HCl buffer solution (with a pH of 8.5) | 0.1 M |

The specific activity of each of TAS, PALDH, and GDH of E. coli HB101 (pUCN18), which serves as a comparative example, was not more than 0.1 U/mg. As such, E. coli HB101 (pUCN18) exhibited virtually no activity of any one of the three enzymes. On the other hand, E. coli HB101 (pNTASPAG) was found to have expressed all the three enzymes. As such, E. coli HB101 (pNTASPAG) exhibited a TAS specific activity of 8 U/mg, a PALDH specific activity of 639 U/mg, and a GDH specific activity of 250 U/mg.

Example 12

Breeding of Recombinant *Escherichia coli* that Expresses MTA

Recombinant E. coli HB101 (pNMTA) was obtained by transforming E. coli HB101 (produced by Takara Bio Inc.)

with use of the recombinant plasmid pNMTA prepared in Example 1. As a comparative example, the recombinant *E. coli* HB101 (pUCN18) explained in Example 8 was used.

Each of the recombinant *E. coli* HB101 (pNMTA) and the recombinant *E. coli* HB101 (pUCN18), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 30° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. The MTA specific activity of the cell-free extract was measured in the same manner as in Example 8.

The specific activity of MTA of *E. coli* HB101 (pUCN18), which serves as a comparative example, was not more than 0.1 U/mg. As such, *E. coli* HB101 (pUCN18) exhibited virtually no activity of MTA. On the other hand, *E. coli* HB101 (pNMTA) was found to have expressed MTA. As such, *E. coli* HB101 (pNTASPAG) exhibited an MTA specific activity of 38 U/mg.

Example 13

Breeding of Recombinant *Escherichia coli* that Expresses PALDH and GDH

Recombinant *E. coli* HB101 (pNPAG) was obtained by transforming *E. coli* HB101 (produced by Takara Bio Inc.) with use of the recombinant plasmid pNPAG prepared in Example 4. As a comparative example, the recombinant *E. coli* HB101 (pUCN18) explained in Example 8 was used.

Each of the recombinant *E. coli* HB101 (pNPAG) and the recombinant *E. coli* HB101 (pUCN18), which serves as a comparative example, was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 33° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. The specific activity of each of PALDH and GDH of the cell-free extract was measured in the same manner as in Example 8.

The specific activity of each of PALDH and GDH of *E. coli* HB101 (pUCN18), which serves as a comparative example, was not more than 0.1 U/mg. As such, *E. coli* HB101 (pUCN18) exhibited virtually no activity of either one of the enzymes. On the other hand, *E. coli* HB101 (pNPAG) was found to have expressed PALDH and GDH. As such, *E. coli* HB101 (pNPAG) exhibited a PALDH specific activity of 1100 U/mg and a GDH activity of 130 U/mg.

Comparative Example 1

Production of (S)-7-methoxy-2-aminotetraline with Use of the Recombinant *Escherichia coli* that Expresses MTA The recombinant *E. coli* HB101 (pNMTA), obtained in Example 12, which expresses MTA was cultured in the same manner as in Example 12. After that, the bacteria were collected by centrifugation, and were then suspended in 10 mM phosphate buffer solution (with a pH of 6.5), whereby a bacterial suspension was obtained in a volume of 5 ml. Such a bacterial suspension was prepared so that total volume was 30 ml.

Into a flask containing 300 mg of a substrate 7-methoxy-2-tetralone, 460 mg of D-glucose, 3 mg of NAD$^+$, 3 ml of 1 M phosphate buffer solution (with a pH of 7), 910 mg of L-alanine, and 4.0 mg of pyridoxal phosphate, 6 ml of the bacterial suspension were poured, and then deionized water was added so that total volume was 30 ml. The resultant product was stirred at 30° C. for 25 hours while being adjusted to a pH of 6.8 by drippage of 5 N aqueous solution of sodium hydroxide. After the reaction, 7-methoxy-2-aminotetraline produced in the reaction liquid was analyzed under the following HPLC conditions, whereby the rate of conversion and optical purity were measured. In the result, it was found that 7-methoxy-2-aminotetraline was produced, but in such a small amount that the rate of conversion into 7-methoxy-2-aminotetraline was 1.5%. The absolute configuration of 7-methoxy-2-aminotetraline was (S), and the optical purity was 74.1% e.e.

[Conditions for Measurement by High-Performance Liquid Chromatography (HPLC)]
  <Quantitative Analysis>
  Column: Cosmosil 5C8-MS (manufactured by Nacalai Tesque, Inc.)
  Eluant: 30 mM potassium phosphate buffer solution (with a pH of 2.5)/acetonitrile/methanol=4/1/1 (by volume)
  Flow rate: 0.9 mL/min.
  Detection: 254 nm
  <Optical Purity Analysis>
  Column: Crownpak CR(+) (manufactured by Daicel Chemical Industries, Ltd.)
  Eluant: aqueous solution of perchloric acid (with a pH of 1.5)/methanol=85/15 (by volume)
  Flow rate: 0.9 mL/min.
  Detection: 220 nm
  Column temperature: 47° C.

(S)-7-methoxy-2-aminotetraline was found to have been produced through the amination reaction of 7-methoxy-2-tetralone by the transaminase MTA with use of L-alanine as an amino donor, but with low productivity (see Example 14 for consideration).

Comparative Example 2

Production of (S)-7-methoxy-2-aminotetraline with Use of the Recombinant *Escherichia coli* that Expresses MTA and a Commercially Available L-Lactate Dehydrogenase To the reaction system of Comparative Example 1, 2 ml (10000 U) of a commercially available pig-heart-derived L-lactate dehydrogenase (produced by Oriental Yeast Co., Ltd.) were added, and then the same reaction was performed as in Comparative Example 1. After the reaction, the rate of conversion into 7-methoxy-2-aminotetraline and the optical purity thereof were measured. In the result, it was found that 7-methoxy-2-aminotetraline was produced, but in such a small amount that the rate of conversion into 7-methoxy-2-aminotetraline was 2.0%. The absolute configuration of 7-methoxy-2-aminotetraline was (S), and the optical purity was 80.1% e.e.

An L-lactate dehydrogenase, which is a type of α-keto acid reductase, was added to and allowed to react with the system of amination reaction of 7-methoxy-2-tetralone by the transaminase MTA with use of L-alanine as an amino donor. However, the rate of conversion into 7-methoxy-2-aminotetraline was as low as 1.7%. No improvement was found in amount produced (see Example 14 for consideration).

Example 14

Production of (S)-7-methoxy-2-aminotetraline with Use of the Recombinant *Escherichia coli* that Expresses MTA and the Recombinant *Escherichia coli* that Co-Expresses PALDH and GDH To the reaction system of Comparative Example 1, 6 ml of a culture fluid of the recombinant *E. coli* HB101 (pNPAG), obtained in Example 13, which co-expressed PALDH and GDH were further added, and then the same reaction was performed as in Comparative Example 1. After the reaction, the rate of conversion into 7-methoxy-2-aminotetraline and the optical purity thereof were measured. In the result, the rate of conversion into 7-methoxy-2-aminotetraline was so high as to be 90.3%. The absolute configuration of 7-methoxy-2-aminotetraline was (S), and the optical purity was 95.6% e.e.

The coexistence of GDH with PALDH, which is a type of α-keto acid reductase, in the amination reaction of 7-methoxy-2-tetralone by the transaminase MTA with use of L-alanine as an amino donor led to dramatic improvement in amount of 7-methoxy-2-aminotetraline produced, thus achieving a high level of productivity.

Example 15

Production of (S)-7-methoxy-2-aminotetraline with Use of the Recombinant *Escherichia coli* that Expresses MTA, PALDH, and GDH (1)

Into a flask containing 300 mg of a substrate 7-methoxy-2-tetralone, 460 mg of D-glucose, 3 mg of NAD$^+$, 910 mg of L-alanine, and 4.0 mg of pyridoxal phosphate, a culture fluid of the recombinant *E. coli* HB101 (pNMTAPAG), obtained in Example 8, which expresses MTA, PALDH, and GDH was added so that total volume was 30 ml. The resultant product was stirred at 30° C. for 20 hours while being adjusted to a pH of 6.8 by drippage of 5 N aqueous solution of sodium hydroxide. The rate of conversion into 7-methoxy-2-aminotetraline after the reaction was 92.3%. The absolute configuration of 7-methoxy-2-aminotetraline was (S), and the optical purity was 97.0% e.e.

The expression of three enzymes MTA, PALDH, and GDH in one recombinant *Escherichia coli* led to slight improvement in amount of (S)-7-methoxy-2-aminotetraline produced, thus achieving a high level of optical purity, in comparison with Example 14.

Example 16

Production of (S)-7-methoxy-2-aminotetraline with Use of the Recombinant *Escherichia coli* that Expresses MTA, PALDH, and GDH (2)

To a flask containing 300 mg of a substrate 7-methoxy-2-tetralone, 460 mg of D-glucose, 3 mg of NAD$^+$, 910 mg of L-alanine, and 4.0 mg of pyridoxal phosphate, a culture fluid of the recombinant *E. coli* HB101 (pNMTA, pSTVPAG), obtained in Example 9, which expresses MTA, PALDH, and GDH was added so that total volume was 30 ml. The resultant product was stirred at 30° C. for 25 hours while being adjusted to a pH of 6.8 by drippage of 5 N aqueous solution of sodium hydroxide. The rate of conversion into 7-methoxy-2-aminotetraline after the reaction was 60.2%. The absolute configuration of 7-methoxy-2-aminotetraline was (S), and the optical purity was 97.1% e.e.

Example 17

Production of (S)—N-Boc-3-amino-pyrrolidine with Use of the Recombinant *Escherichia coli* that Expresses MTA, PALDH, and GDH To a flask containing 1.25 g of a substrate N-Boc-3-pyrrolidinone, 1.82 g of D-glucose, 10 mg of NAD$^+$, 3.61 g of L-alanine, and 4.0 mg of pyridoxal phosphate, a culture fluid of the recombinant *E. coli* HB101 (pNMTAPAG), obtained in Example 8, which expresses MTA, PALDH, and GDH was added so that total volume was 25 ml. The resultant product was stirred at 30° C. while being adjusted to a pH of 6.8 by drippage of 5 N aqueous solution of sodium hydroxide.

After 2.5 hours in reaction, 0.625 g of N-Boc-3-pyrrolidinone, 0.91 g of D-glucose, 1.8 g of L-alanine, and 3.3 mg of pyridoxal phosphate were added. Further, after five hours in reaction, 0.625 g of N-Boc-3-pyrrolidinone, 0.91 g of D-glucose, and 3.3 mg of pyridoxal phosphate were added. Furthermore, after nine hours in reaction, 0.25 g of N-Boc-3-pyrrolidinone, 0.36 g of D-glucose, 19 mg of NAD$^+$, and 3.3 mg of pyridoxal phosphate were added. During the reaction, the reaction liquid was sampled. From the sample, N-Boc-3-aminopyrrolidine was extracted by the addition of ethyl acetate after basifying the sample with 6 N aqueous solution of sodium hydroxide. The amount of N-Boc-3-aminopyrrolidine produced was measured by analyzing N-Boc-3-aminopyrrolidine under the following GC conditions. Further, by the law of the art, N-Boc-3-aminopyrrolidine thus obtained was acted on by 3,5-dinitrobenzyl chloride to form a dinitrobenzyl derivative. After that, the dinitrobenzyl derivative was analyzed under the following HPLC conditions, whereby the optical purity thereof was measured. In the result, the amount of N-Boc-3-aminopyrrolidine produced after 23 hours in reaction was 2.14 g. The absolute configuration of N-Boc-3-aminopyrrolidine was (S), and the optical purity was 99.4% e.e.

[Conditions for Quantitative Analysis by Gas Chromatography (GC)]
Column: Rtx-5 Amine (30 m, 0.25 mm ID) (manufactured by Restek Corporation)
Column temperature: 150° C.
Inlet temperature: 250° C.
Detector temperature: 250° C.
Detection: FID
Carrier gas: He, 150 kPa
Elution time: N-Boc-3-pyrrolidinone (9.2 min.)
N-Boc-3-aminopyrrolidine (11.5 min.)
[Conditions for Optical Purity Measurement by High-Performance Liquid Chromatography (HPLC)]
Column: Chiralpak AD-H (manufactured by Daicel Chemical Industries, Ltd.)
Eluant: n-hexane/ethanol/diethylamine=75/25/0.1 (by volume)
Flow rate: 0.7 mL/min.
Detection: 240 nm Column temperature: 40° C.
Elution time: S (15.0 min.), R (8.9 min.)

Example 18

Production of (R)—N-Boc-3-aminopyrrolidine with Use of the Recombinant *Escherichia coli* that Expresses TAS, PALDH, and GDH To a flask containing 0.5 g of a substrate N-Boc-3-pyrrolidinone, 0.73 g of D-glucose, 4 mg of NAD$^+$, 1.44 g of D-alanine, and 3.3 mg of pyridoxal phosphate, a culture fluid of the recombinant *E. coli* HB101 (pNTASPAG), obtained in Example 11, which expresses TAS, PALDH, and GDH was added so that total volume was 25 ml. The resultant product was stirred at 30° C. while being adjusted to a pH of 6.8 by drippage of 5 N aqueous solution of sodium hydroxide. After nine hours in reaction, 0.25 g of N-Boc-3-pyrrolidinone, 0.37 g of D-glucose, 0.37 g of D-alanine, and 3 mg of pyridoxal phosphate were added.
The amount of N-Boc-3-aminopyrrolidine produced after 23 hours in reaction and the optical purity thereof were measured according to the method described in Example 17. In the result, the amount produced was 0.54 g. The absolute configuration of N-Boc-3-aminopyrrolidine was (R), and the optical purity was not less than 99.9% e.e.

Example 19

Production of (S)—N-Boc-3-aminopiperidine with Use of the Recombinant *Escherichia coli* that Expresses MTA, PALDH, and GDH To a flask containing 1.25 g of a substrate N-Boc-3-piperidinone, 1.7 g of D-glucose, 9 mg of NAD$^+$, 3.36 g of L-alanine, and 3.3 mg of pyridoxal phosphate, a culture fluid of the recombinant *E. coli* HB101 (pNMTAPAG), obtained in Example 8, which expresses MTA, PALDH, and GDH was added so that total volume was 25 ml. The resultant product was stirred at 30° C. while being adjusted to a pH of 6.8 by drippage of 5 N aqueous solution of sodium hydroxide.
After two hours in reaction, 1.25 g of N-Boc-3-piperidinone, 1.7 g of D-glucose, 1.0 g of L-alanine, and 3.3 mg of pyridoxal phosphate were added. Further, after five hours in reaction, 1.25 g of N-Boc-3-piperidinone, 1.7 g of D-glucose, and 3.3 mg of pyridoxal phosphate were added. During the reaction, the reaction liquid was sampled. From the sample, N-Boc-3-aminopiperidine was extracted by the addition of ethyl acetate after basifying the sample with 6 N aqueous solution of sodium hydroxide. The amount of N-Boc-3-aminopiperidine produced was measured by analyzing N-Boc-3-aminopiperidine under the following GC conditions. Further, by the law of the art, N-Boc-3-aminopiperidine thus obtained was acted on by 3,5-dinitrobenzyl chloride to form a dinitrobenzyl derivative. After that, the dinitrobenzyl derivative was analyzed under the following HPLC conditions, whereby the optical purity thereof was measured. In the result, the amount of N-Boc-3-aminopyrrolidine produced after 23.5 hours in reaction was 3.13 g. The absolute configuration of N-Boc-3-aminopyrrolidine was (S), and the optical purity was not less than 99.9% e.e.

[Conditions for Quantitative Analysis by Gas Chromatography (GC)]
Column: Rtx-5 Amine (30 m, 0.25 mm ID) (manufactured by Restek Corporation)
Column temperature: 150° C.
Inlet temperature: 250° C.
Detector temperature: 250° C.
Detection: FID
Carrier gas: He, 150 kPa
Elution time: N-Boc-3-piperidinone (13.2 min.)
N-Boc-3-aminopiperidine (12.5 min.)
[Conditions for Optical Purity Measurement by High-Performance Liquid Chromatography (HPLC)]
Column: Chiralpak AD-H (manufactured by Daicel Chemical Industries, Ltd.)
Eluant: n-hexane/ethanol/diethylamine=75/25/0.1 (by volume)
Flow rate: 0.7 mL/min.
Detection: 240 nm
Column temperature: 40° C.
Elution time: S (19.1 min.), R (7.7 min.)

Example 20

Production of (S)—N-Boc-3-aminopiperidine with Use of the Recombinant *Escherichia coli* that Expresses TPS, PALDH, and GDH To a flask containing 0.6 g of a substrate N-Boc-3-piperidinone, 0.82 g of D-glucose, 4 mg of NAD$^+$, 1.62 g of L-alanine, and 4.0 mg of pyridoxal phosphate, a culture fluid of the recombinant *E. coli* HB101 (pNTPSPAG), obtained in Example 10, which expresses TPS, PALDH, and GDH was added so that total volume was 30 ml. The resultant product was stirred at 30° C. for 20 hours while being adjusted to a pH of 6.8 by drippage of 5 N aqueous solution of sodium hydroxide. The amount of N-Boc-aminopiperidine produced and the optical purity thereof were measured according to the method described in Example 19. In the result, the amount produced was 0.54 g. The absolute configuration of N-Boc-aminopiperidine was (S), and the optical purity was 99.4% e.e.

Example 21

Production of (R)—N-benzyl-3-aminopiperidine with Use of the Recombinant *Escherichia coli* that Expresses TAS, PALDH, and GDH To a separable flask containing 26.9 g of a substrate N-benzyl-3-piperidinone hydrochloride, 32.2 g of D-glucose, 79 mg of NAD$^+$, 63.7 g of D-alanine, and 75 mg of pyridoxal phosphate, 564 ml of a culture fluid of the *E. coli* HB101 (pNTASPAG), obtained in Example 11, which expresses TAS, PALDH, and GDH were added. The resultant product was stirred at 30° C. while being adjusted to a pH of 6.8 by drippage of 5 N aqueous solution of sodium hydroxide.
During the reaction, the reaction liquid was sampled. From the sample, N-benzyl-3-aminopiperidine was extracted by the addition of ethyl acetate after basifying the sample with 6 N aqueous solution of sodium hydroxide. The amount of N-benzyl-3-aminopiperidine produced was measured by analyzing N-benzyl-3-aminopiperidine under the following HPLC conditions. Further, by the law of the art, N-benzyl-3-aminopiperidine thus obtained was acted on by 3,5-dinitrobenzyl chloride to form a dinitrobenzyl derivative. After that, the dinitrobenzyl derivative was analyzed under the following HPLC conditions, whereby the optical purity thereof was measured. In the result, the amount of N-benzyl-3-aminopiperidine produced after 20 hours in reaction was 20.2 g. The absolute configuration of N-benzyl-3-aminopiperidine was (R), and the optical purity was not less than 99.9% e.e.

[Conditions for Measurement by High-Performance Liquid Chromatography (HPLC)]
<Quantitative Analysis>
Column: Finepak SIL C18-T (manufactured by JASCO Corporation)
Eluant: water/acetonitrile/KH$_2$PO$_4$/SDS=1260 ml/740 ml/10 g/2.88 g
Adjusted to a pH of 3.6 with phosphoric acid after mixing
Flow rate: 1.0 mL/min.
Detection: 210 nm
Column temperature: 30° C.
<Optical Purity Analysis>
Column: Chiralpak AD-H (manufactured by Daicel Chemical Industries, Ltd.)
Eluant: n-hexane/ethanol/diethylamine=75/25/0.1 (by volume)
Flow rate: 0.7 mL/min.
Detection: 240 nm
Column temperature: 40° C.
Elution time: R (9.6 min.), S (14.4 min.)

After the reaction liquid had been adjusted to a pH of 13 by the addition of 5 N aqueous solution of sodium hydroxide, N-benzyl-3-aminopiperidine was extracted with 1 L of toluene, and was then further extracted from the aqueous phase with 1 L of toluene. After the solvent had been distilled under reduced pressure away from a combination of the organic phases thus obtained, (R)—N-benzyl-3-aminopiperidine was purified by distillation. Thus, 17.7 g of (R)—N-benzyl-3-aminopiperidine were obtained in the form of colorless oil.

Example 22

Production of (R)-1-(3,4-dimethoxyphenyl)-2-aminopropane with Use of the Recombinant *Escherichia coli* that Expresses TAS, PALDH, and GDH To a flask containing 1.5 g of a substrate 1-(3,4-dimethoxyphenyl)-2-propanone, 4.17 g of D-glucose, 5.1 mg of NAD$^+$, 4.13 g of D-alanine, and 4.0 mg of pyridoxal phosphate, 30 ml of a culture fluid of the *E. coli* HB101 (pNTASPAG), obtained in Example 11, which expresses TAS, PALDH, and GDH were added. The resultant product was stirred at 30° C. while being adjusted to a pH of 6.8 by drippage of 5 N aqueous solution of sodium hydroxide.

After ten hours in reaction, 1.5 g of a substrate 1-(3,4-dimethoxyphenyl)-2-propanone, 4.17 g of D-glucose, 4.13 g of D-alanine, and 3.3 mg of pyridoxal phosphate were added. During the reaction, the reaction liquid was sampled. From the sample, 1-(3,4-dimethoxyphenyl)-2-aminopropane was extracted by the addition of ethyl acetate after basifying the sample with 6 N aqueous solution of sodium hydroxide. The amount of 1-(3,4-dimethoxyphenyl)-2-aminopropane produced was measured by analyzing 1-(3,4-dimethoxyphenyl)-2-aminopropane under the following HPLC conditions. Further, by the law of the art, 1-(3,4-dimethoxyphenyl)-2-aminopropane thus obtained was acted on by 3,5-dinitrobenzyl chloride to form a dinitrobenzyl derivative. After that, the dinitrobenzyl derivative was analyzed under the following HPLC conditions, whereby the optical purity thereof was measured. In the result, the amount of 1-(3,4-dimethoxyphenyl)-2-aminopropane produced after 27 hours in reaction was 2.42 g. The absolute configuration of 1-(3,4-dimethoxyphenyl)-2-aminopropane was (R), and the optical purity was not less than 99.9% e.e.

[Conditions for Measurement by High-Performance Liquid Chromatography (HPLC)]
<Quantitative Analysis>
Column: J'sphere ODS-H80 (manufactured by YMC Co., Ltd.)
Eluant: water/acetonitrile/KH$_2$PO$_4$/sodium hexasulfonate=1000 ml/200 ml/3.15 g/1.13 g
Adjusted to a pH of 2.5 with phosphoric acid after mixing
Flow rate: 1.0 mL/min.
Detection: 240 nm
Column temperature: 40° C.
<Optical Purity Analysis>
Column: Chiralpak AD-H (manufactured by Daicel Chemical Industries, Ltd.)
Eluant: n-hexane/ethanol/diethylamine=75/25/0.1 (by volume)
Flow rate: 1.0 mL/min.
Detection: 240 nm
Column temperature: 40° C.
Elution time: R (7.2 min.), S (10.2 min.)

Example 23

Production of (R)-1-(4-methoxyphenyl)-2-aminopropane with Use of the Recombinant *Escherichia coli* that Expresses TAS, PALDH, and GDH To a flask containing 1.5 g of a substrate 1-(4-methoxyphenyl)-2-propanone, 4.94 g of D-glucose, 6.1 mg of NAD$^+$, 4.88 g of D-alanine, and 4.0 mg of pyridoxal phosphate, 30 ml of a culture fluid of the *E. coli* HB101 (pNTASPAG), obtained in Example 11, which expresses TAS, PALDH, and GDH were added. The resultant product was stirred at 30° C. while being adjusted to a pH of 6.8 by drippage of 5 N aqueous solution of sodium hydroxide. During the reaction, the reaction liquid was sampled. From the sample, 1-(4-methoxyphenyl)-2-aminopropane was extracted by the addition of ethyl acetate after basifying the sample with 6 N aqueous solution of sodium hydroxide. The amount of 1-(4-methoxyphenyl)-2-aminopropane produced was measured by analyzing 1-(4-methoxyphenyl)-2-aminopropane under the following HPLC conditions. Further, by the law of the art, 1-(4-methoxyphenyl)-2-aminopropane thus obtained was acted on by 3,5-dinitrobenzyl chloride to form a dinitrobenzyl derivative. After that, the dinitrobenzyl derivative was analyzed under the following HPLC conditions, whereby the optical purity thereof was measured.

In the result, the amount of 1-(4-methoxyphenyl)-2-aminopropane produced after 68 hours in reaction was 1.48 g. The absolute configuration of 1-(4-methoxyphenyl)-2-aminopropane was (R), and the optical purity was 99.6% e.e.

[Conditions for Measurement by High-Performance Liquid Chromatography (HPLC)]
<Quantitative Analysis>
Column: J'sphere ODS-H80 (manufactured by YMC Co., Ltd.)
Eluant: water/acetonitrile/KH$_2$PO$_4$/sodium hexasulfonate=1000 ml/200 ml/3.15 g/1.13 g
Adjusted to a pH of 2.5 with phosphoric acid after mixing
Flow rate: 1.0 mL/min.
Detection: 240 nm
Column temperature: 40° C.
<Optical Purity Analysis>

Column: Chiralpak AD-H (manufactured by Daicel Chemical Industries, Ltd.)
Eluant: n-hexane/ethanol/diethylamine=75/25/0.1 (by volume)
Flow rate: 1.0 mL/min.
Detection: 240 nm
Column temperature: 40° C.
Elution time: R (7.8 min.), S (14.8 min.)

Example 24

Production of (R)—N-benzyl-3-aminopyrrolidine with Use of the Recombinant *Escherichia coli* that Expresses TAS, PALDH, and GDH To a flask containing 0.6 g of a substrate N-benzyl-3-pyrrolidinone, 1.85 g of D-glucose, 2.3 mg of $NAD^+$, 1.83 g of D-alanine, and 4.0 mg of pyridoxal phosphate, 30 ml of a culture fluid of the *E. coli* HB101 (pNTASPAG), obtained in Example 11, which expresses TAS, PALDH, and GDH were added. The resultant product was stirred at 30° C. while being adjusted to a pH of 6.8 by drippage of 5 N aqueous solution of sodium hydroxide. During the reaction, the reaction liquid was sampled. From the sample, N-benzyl-3-aminopyrrolidine was extracted by the addition of ethyl acetate after basifying the sample with 6 N aqueous solution of sodium hydroxide. The amount of N-benzyl-3-aminopyrrolidine produced was measured by analyzing N-benzyl-3-aminopyrrolidine under the following HPLC conditions. Further, by the law of the art, N-benzyl-3-aminopyrrolidine thus obtained was acted on by 3,5-dinitrobenzyl chloride to form a dinitrobenzyl derivative. After that, the dinitrobenzyl derivative was analyzed under the following HPLC conditions, whereby the optical purity thereof was measured.

In the result, the amount of N-benzyl-3-aminopyrrolidine produced after 24 hours in reaction was 0.48 g. The absolute configuration of N-benzyl-3-aminopyrrolidine was (R), and the optical purity was not less than 99.9% e.e.

[Conditions for Measurement by High-Performance Liquid Chromatography (HPLC)]
<Quantitative Analysis>
Column: Finepak SIL C18-T (manufactured by JASCO Corporation)
Eluant: water/acetonitrile/$KH_2PO_4$/SDS=1260 ml/740 ml/10 g/2.88 g
Adjusted to a pH of 3.6 with phosphoric acid after mixing
Flow rate: 1.0 mL/min.
Detection: 210 nm
Column temperature: 30° C.
<Optical Purity Analysis>
Column: Chiralpak AD-H (manufactured by Daicel Chemical Industries, Ltd.)
Eluant: n-hexane/ethanol/diethylamine=75/25/0.1 (by volume)
Flow rate: 1.5 mL/min.
Detection: 240 nm
Column temperature: 40° C.
Elution time: R (7.3 min.), S (14.9 min.)

Example 25

Production of (S)-2-aminoheptane with Use of the Recombinant *Escherichia coli* that Expresses MTA, PALDH, and GDH To a flask containing 0.2 g of a substrate 2-heptanone, 480 g of D-glucose, 5 mg of $NAD^+$, 0.94 g of L-alanine, and 2.0 mg of pyridoxal phosphate, a culture fluid of the recombinant *E. coli* HB101 (pNMTAPAG), obtained in Example 8, which expresses MTA, PALDH, and GDH was added so that total volume was 10 ml. The resultant product was stirred at 30° C. while being adjusted to a pH of 6.8 by drippage of 5 N aqueous solution of sodium hydroxide.

During the reaction, the reaction liquid was sampled. From the sample, 2-aminoheptane was extracted by the addition of ethyl acetate after basifying the sample with 6 N aqueous solution of sodium hydroxide. The amount of 2-aminoheptane produced was measured by analyzing 2-aminoheptane under the following GC conditions. Further, by the law of the art, 2-aminoheptane thus obtained was acted on by 3,5-dinitrobenzyl chloride to form a dinitrobenzyl derivative. After that, the dinitrobenzyl derivative was analyzed under the following HPLC conditions, whereby the optical purity thereof was measured. In the result, the rate of conversion into 2-aminoheptane produced after 20 hours in reaction was 98%. The absolute configuration of 2-aminoheptane was (S), and the optical purity was 98.8% e.e.

[Conditions for Quantitative Analysis by Gas Chromatography (GC)]
Column: Rtx-5 Amine (30 m, 0.25 mm ID) (manufactured by Restek Corporation)
Column temperature: 50° C.
Inlet temperature: 250° C.
Detector temperature: 300° C.
Detection: FID
Carrier gas: He, 150 kPa
Elution time: 2-heptanone (15.2 min.)
2-aminoheptane (14.0 min.)
[Conditions for Optical Purity Measurement by High-Performance Liquid Chromatography (HPLC)]
Column: Chiralpak AD-H (manufactured by Daicel Chemical Industries, Ltd.)
Eluant: n-hexane/ethanol/diethylamine=90/10/0.1 (by volume)
Flow rate: 1.0 mL/min.
Detection: 240 nm
Column temperature: 35° C.
Elution time: S (15.3 min.), R (9.3 min.)

Example 26

Production of (R)-2-aminoheptane with Use of the Recombinant *Escherichia coli* that Expresses TAS, PALDH, and GDH To a flask containing 0.2 g of a substrate 2-heptanone, 480 g of D-glucose, 5 mg of $NAD^+$, 0.94 g of L-alanine, and 2.0 mg of pyridoxal phosphate, a culture fluid of the recombinant *E. coli* HB101 (pNTASPAG), obtained in Example 11, which expresses TAS, PALDH, and GDH was added so that total volume was 10 ml. The resultant product was stirred at 30° C. while being adjusted to a pH of 6.8 by drippage of 5 N aqueous solution of sodium hydroxide.

The rate of conversion into 2-aminoheptane and the optical purity thereof were measured according to the method described in Example 25. In the result, the rate of conversion was 97.5%. The absolute configuration of 2-aminoheptane was (R), and the optical purity was not less than 99.9% e.e.

Example 27

Production of (S)-2-aminoheptane with Use of the Recombinant *Escherichia coli* that Expresses TPS, PALDH, and GDH To a flask containing 0.2 g of a substrate 2-heptanone, 480 g of D-glucose, 5 mg of $NAD^+$, 0.94 g of L-alanine, and 2.0 mg of pyridoxal phosphate, a culture fluid of the recombinant *E. coli* HB101 (pNTPSPAG), obtained in Example 10, which expresses TPS, PALDH, and GDH was added so that total volume was 10 ml. The resultant product was stirred at 30° C. while being adjusted to a pH of 6.8 by drippage of 5 N aqueous solution of sodium hydroxide.

The rate of conversion into 2-aminoheptane and the optical purity thereof were measured according to the method described in Example 25. In the result, the rate of conversion was 97.5%. The absolute configuration of 2-aminoheptane was (S), and the optical purity was 97.7% e.e.

Example 28

Building of a Recombinant Vector (pNMTAPAF) Containing Three Structural Genes, Namely MAT, PALDH, and a Formate Dehydrogenase FDH Derived from *Thiobacillus* sp. Strain KNK65MA (FERM BP-7671)

(28-1. Building of an Expression Vector (pNF) Containing a Formate Dehydrogenase Gene)

Primer 19 (SEQ ID NO: 27 of the Sequence Listing) and Primer 20 (SEQ ID NO: 28 of the Sequence Listing) were used to perform a PCR for which a plasmid pFT002 (that can be obtained and prepared by a person skilled in the art according to a method described in International Publication No. 2003/031626) served as a template. Thus obtained was duplex DNA in which a ribosome binding sequence of *Escherichia coli* had been added five bases upstream of a start codon of a formate dehydrogenase (hereinafter referred to as "FDH") gene derived from *Thiobacillus* sp. strain KNK65MA (FERM BP-7671), an KpnI cleavage site had been added immediately before the ribosome binding sequence of *Escherichia coli*, and an SphI cleavage site had been added immediately after a stop codon. The FDH is an example of the "enzyme (C)" of the present invention.

The DNA fragment thus obtained was digested with KpnI and SphI, and was then inserted between a KpnI cleavage site and an SphI cleavage site downstream of a lac promoter of a plasmid pUCN18 (a plasmid in which an NdeI cleavage site had been destructed by altering the 185th T of pUC18 (produced by Takara Bio Inc., GenBank Accession No. L09136) to A by a PCR method and into which a new NdeI cleavage site had been introduced by further altering the 471st and 472nd GC to TG). Thus built was a recombinant vector pNF.

(28-2. Building of an Expression Vector pNPAF Containing a PALDH Structural Gene and an FDH Structural Gene)

Primer 21 (SEQ ID NO: 29 of the Sequence Listing) and Primer 22 (SEQ ID NO: 30 of the Sequence Listing) were used to perform a PCR for which the chromosome DNA, obtained in Example 4, of *Pediococcus acidilactici* strain JCM8797 served as a template. Thus obtained was duplex DNA in which an NdeI cleavage site had been added to a start codon of a gene consisting of the base sequence represented by SEQ ID NO: 19 and a KpnI cleavage site had been added immediately after a stop codon. The PCR was performed by using a TaKaRa Pyrobest (produced by Takara Bio Inc.) as a DNA polymerase, and the reaction conditions were in conformity with an instruction manual therefor. The DNA was partially digested with NdeI and KpnI, and was then inserted between an NdeI cleavage site and a KpnI cleavage site of the already-prepared recombinant vector pNF. Thus built was a recombinant vector pNPAF.

(28-3. Building of a Recombinant Vector (pNMTAPAF) Containing Three Structural Genes, Namely MAT, PALDH, and FDH)

Figure 4:
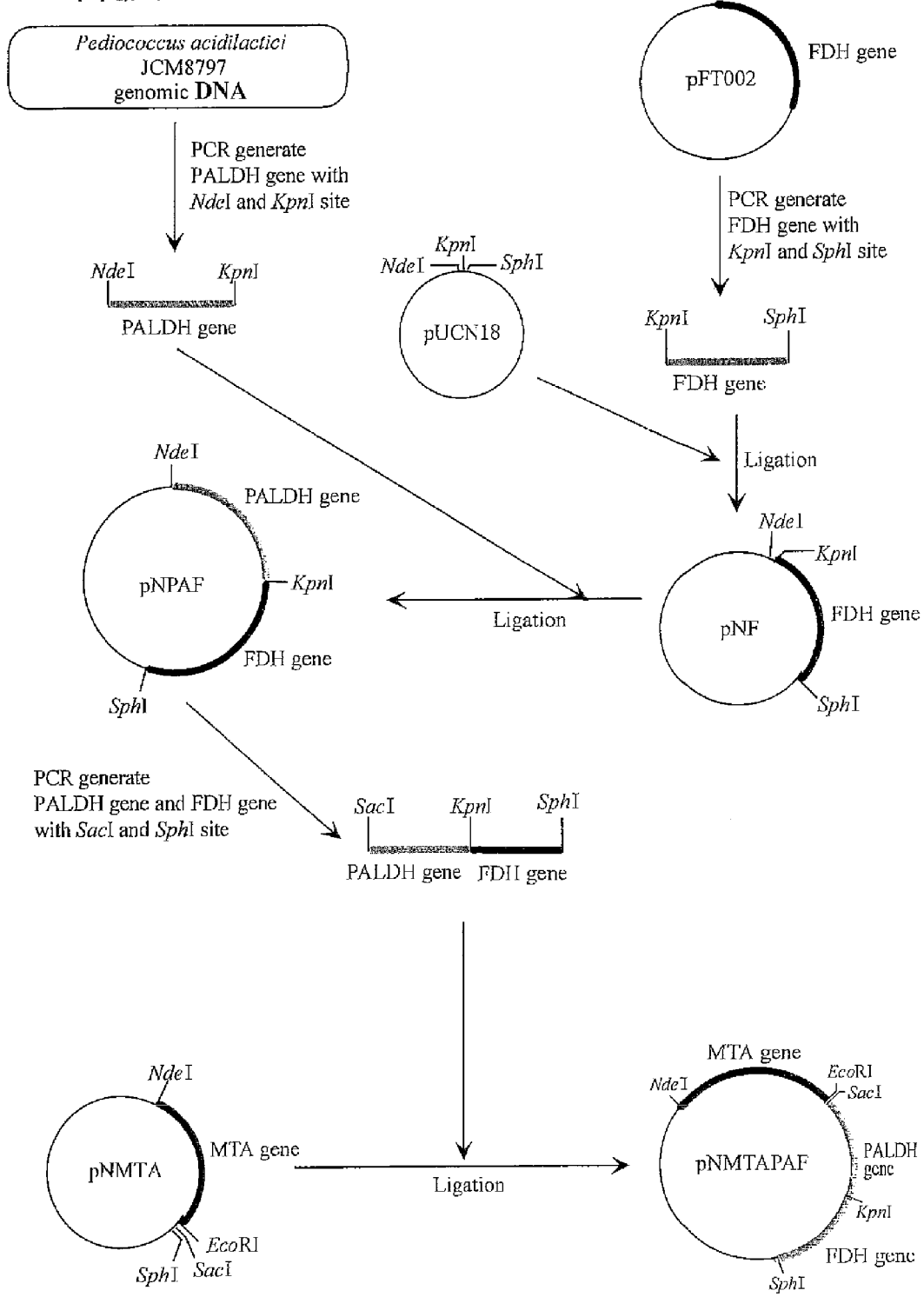
FIG. 4 is a schematic diagram of respective procedures for building recombinant plasmids pNF, pNPAF, and pNMTAPAF.

Primer 23 (SEQ ID NO: 31 of the Sequence Listing) and Primer 20 (SEQ ID NO: 28 of the Sequence Listing) were used to perform a PCR for which the recombinant vector pNPAF thus prepared served as a template. Thus obtained was duplex DNA in which a ribosome binding sequence of *Escherichia coli* had been added five bases upstream of a start codon of the PALDH structural gene, an SacI cleavage site had been added immediately before the ribosome binding sequence of *Escherichia coli*, an SphI cleavage site had been added immediately after a stop codon of the FDH structural gene, and the PALDH structural gene and the FDH structural gene had been bonded together. The duplex DNA was digested with SacI and SphI, and was then inserted between an SacI cleavage site and an SphI cleavage site of the recombinant vector pNMTA obtained in Example 1. Thus built was a recombinant vector pNMTAPAF. FIG. 4 shows a simple illustration of the procedure for building the recombinant vector pNMTAPAF.

Example 29

Breeding of Recombinant *Escherichia coli* that Expresses MTA, PALDH, and FDH

Recombinant *E. coli* HB101 (pNMTAPAF) was obtained by transforming *E. coli* HB101 (produced by Takara Bio Inc.) with use of the recombinant plasmid pNMTAPAF prepared in Example 28. Each of the recombinant *E. coli* HB101 (pNMTAPAF) and the recombinant *E. coli* HB101 (pUCN18), obtained in Example 8, which serves as a comparative example was inoculated in 50 ml of a 2×YT culture medium (tryptone 1.6%, yeast extract 1.0%, NaCl 0.5%, with a pH of 7.0) containing 200 μg/ml of ampicillin, and was then cultured with shaking at 32° C. for 24 hours. The bacteria thus cultured were collected by centrifugation, and were then suspended in 50 ml of 100 mM phosphate buffer solution (with a pH of 6.5). The bacteria were grounded with use of an Ultrasonic Homogenizer UH-50 (manufactured by SMT Co., Ltd.). After that, the residual bacteria were removed by centrifugation. Thus obtained was a cell-free extract. Specific activity was calculated by measuring each of the MAT activity, PALDH activity, and FDH activity of the cell-free extract. The MTA activity and the PALDH activity were measured in the same manners as in Example 8. Further, the FDH activity was measured in the following manner. It should be noted that the concentration of protein in the cell-free extract was measured with use of a protein assay kit (manufactured Bio-Rad Laboratories).

(How to Measure the FDH Activity)

The FDH activity was calculated from the rate of increase in absorbance at 340 nm of a reaction liquid, obtained by dissolving a formic acid and a coenzyme $NAD^+$ in 100 mM phosphate buffer solution (with a pH of 7) so that the formic acid had a final concentration of 0.5 M and the coenzyme $NAD^+$ had a final concentration of 2 mM and by further adding an enzyme solution, which had reacted at 30° C. for one minute. Under the present reaction conditions, the enzyme activity with which 1 μmol of $NAD^+$ had been reduced to NADH per minute was defined as 1 U.

The specific activity of each of MTA, PALDH, and FDH of *E. coli* HB101 (pUCN18), which serves as a comparative example, was not more than 0.1 U/mg. As such, *E. coli* HB101 (pUCN18) exhibited virtually no activity of any one of the three enzymes. On the other hand, *E. coli* HB101

(pNMTAPAF) was found to have expressed all the three enzymes. As such, *E. coli* HB101 (pNMTAPAF) exhibited an MTA specific activity of 25 U/mg, a PALDH specific activity of 820 U/mg, and an FDH specific activity of 15 U/mg.

Example 30

Production of (S)-7-methoxy-2-aminotetraline with Use of Recombinant *Escherichia coli* that Expresses MTA, PALDH, and FDH Into a flask containing 520 mg of a substrate 7-methoxy-2-tetralone, 10 mg of sodium formate, 3 mg of NAD$^+$, 1.57 mg of L-alanine, and 20 mg of pyridoxal phosphate, a culture fluid of the recombinant *E. coli* HB101 (pNMTAPAF), obtained in Example 29, which expresses MTA, PALDH, and FDH was added so that total volume was 30 ml. The resultant product was stirred at 35° C. for 28 hours while being adjusted to a pH of 6.3 by drippage of 5 N aqueous solution of formic acid. The rate of conversion into 7-methoxy-2-aminotetraline after the reaction was 92.6%. The absolute configuration of 7-methoxy-2-aminotetraline was (S), and the optical purity was 98.1% e.e.

The coexistence of FDH with PALDH, which is a type of α-keto acid reductase, in the amination reaction of 7-methoxy-2-tetralone by the transaminase MTA with use of L-alanine as an amino donor led to dramatic improvement in amount of 7-methoxy-2-aminotetraline produced, thus achieving a high level of productivity (in comparison with Comparative Example 2)

The invention claimed is:

1. A method for producing an optically-active amine compound in a reaction system comprising at least three enzymes and a ketone compound, wherein said enzymes are:
   (A) a transaminase which uses an α-amino acid as an amino-group donor and which acts on the ketone compound to convert the ketone compound into the optically-active amine compound, and to convert the α-amino acid into an α-keto acid;
   (B) an α-keto acid reductase, which uses a reduced β-nicotinamide adenine dinucleotide (NADH) or a reduced β-nicotinamide adenine dinucleotide phosphate (NADPH) as a coenzyme and which reduces, to an α-hydroxy acid, the α-keto acid produced from reaction with the transaminase of (A) and which does not act on the ketone compound; and
   (C) an enzyme that converts oxidized β-nicotinamide adenine dinucleotide (NAD+) produced from the NADH resulting from action of the α-keto acid reductase of (B) to NADH, or that converts oxidized β-nicotinamide adenine dinucleotide phosphate (NADP+) produced from the NADPH resulting from the action of the α-keto acid reductase (B) into NADPH;
   to convert the ketone compound into a corresponding optically-active amine compound in which a carbon atom with an amino group bonded thereto serves as an asymmetric point.

2. The method as set forth in claim 1, wherein the enzymes are:
   (A) a transaminase which uses α-alanine as an amino-group donor and which acts on the ketone compound to convert the ketone compound into a corresponding optically-active amine compound in which a carbon atom with an amino group bonded thereto serves as an asymmetric point;
   (B) an α-keto acid reductase which uses a reduced β-nicotinamide adenine dinucleotide (NADH) as a coenzyme and which reduces pyruvic acid produced from the α-alanine through action of the transaminase (A) to a lactic acid, and which does not act on the ketone compound; and
   (C) an enzyme that converts oxidized β-nicotinamide adenine dinucleotide (NAD+) produced from the NADH through action of the α-keto acid reductase (B) into NADH.

3. The method as set forth in claim 1, wherein the enzyme source is a transformant obtained by introducing DNA molecules respectively coding for the enzymes (A) to (C), and/or a product of culture thereof.

4. The method as set forth in claim 1, wherein the enzyme source is a transformant obtained by transforming a host cell with either a plurality of recombinant vectors separately containing and expressing DNA molecules respectively coding for the enzymes (A) to (C) or with a single recombinant vector containing and expressing all the DNA molecules respectively coding for the enzymes (A) to (C) and/or a product of culture thereof.

5. The method as set forth in claim 1, wherein the enzyme (B) is a lactate dehydrogenase and the enzyme (C) is a glucose dehydrogenase or a formate dehydrogenase.

6. The method as set forth in claim 1, wherein the enzyme (B) is an enzyme derived from a microorganism belonging to *Pediococcus acidilactici*.

7. The method as set forth in claim 1, wherein the enzyme (C) is an enzyme derived from a microorganism belonging to *Bacillus megaterium* or *Thiobacillus* sp.

8. The method as set forth in claim 1, wherein the transaminase (A) is an enzyme derived from a microorganism belonging to the genus *Pseudomonas* or the genus *Arthrobacter*.

9. The method as set forth in claim 8, wherein the transaminase (A) is an enzyme derived from *Pseudomonas fluorescens* strain KNK08-18 (FERM BP-10599), *Pseudomonas* sp, strain KNK425 (FERM BP-6525), or *Arthrobacter* sp, strain KNK168 (FERM BP-5228).

10. The method as set forth in claim 1, wherein the transaminase (A) is a polypeptide as set forth in any one of (a) or (b):
    (a) a polypeptide as set forth in SEQ ID NO: 25;
    (b) a polypeptide having at least 85% homology with SEQ ID NO: 25 of the Sequence Listing.

11. The method as set forth in claim 1, wherein the transaminase (A) is a polypeptide coded for by a polynucleotide as set forth in SEQ ID NO: 26.

12. The method as set forth in claim 1, wherein the ketone compound is represented by general formula (1)

(1)

where R1 and R2 are each a substitutable alkyl group, a substitutable aralkyl group, or a substitutable aryl group, or are different in structure but bonded to each other to form a ring, and the corresponding optically-active amino compound is represented by general formula (2)

(2)

where R1 and R2 are as defined in general formula (1) and the mark * indicates an asymmetric carbon atom.

* * * * *

SEQUENCE LISTING

<160> NUMBER OF SEQ ID NOS: 31

<210> SEQ ID NO 1
<211> LENGTH: 449
<212> TYPE: PRT
<213> ORGANISM: Pseudomonas sp.

<400> SEQUENCE: 1

```
Met Tyr Glu Gln Tyr Lys Thr Ala Gln Lys Lys Phe Trp His Pro Met
1               5                   10                  15

Ser Ser Ser Ala Pro Ala Asn Arg Ser Lys Thr Leu Ile Ile Ala Arg
            20                  25                  30

Gly Asp Gly Asn Tyr Val Thr Asp Ile Glu Gly His Arg Met Leu Asp
        35                  40                  45

Gly Val Gly Gly Leu Trp Asn Val Asn Val Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Ser Met Phe Ala Gln Glu Asn Met Thr Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Pro Leu Leu Ala Gly Cys His
                165                 170                 175

Leu Leu Asp Thr Pro Trp Leu Tyr Arg Asn Pro Trp Asp Cys Arg Asp
            180                 185                 190

Pro Glu Glu Leu Thr Ala His Cys Ile Arg Gln Leu Glu Asp Gln Ile
        195                 200                 205

Ala Leu Leu Gly Pro Gln Thr Ile Ala Ala Leu Ile Ala Glu Pro Val
    210                 215                 220

Gln Gly Ala Gly Gly Val Ile Val Pro Pro Ala Tyr Tyr Trp Lys Gly
225                 230                 235                 240

Leu Arg Glu Val Cys Asp Arg His Gly Ile Leu Leu Ile Ala Asp Glu
                245                 250                 255
```

```
Val Val Thr Gly Phe Gly Arg Thr Gly Cys Met Leu Gly Ser Arg Gly
            260                 265                 270

Trp Gly Val Ala Pro Asp Val Leu Cys Leu Ala Lys Gly Ile Thr Ala
            275                 280                 285

Gly Tyr Ile Pro Met Gly Ala Thr Val Phe Asn Gln Arg Met Val Asp
            290                 295                 300

Ala Ile Glu Asn Gly Pro Gly Phe Ser Asn Val Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Gly Lys Ile Gly
            340                 345                 350

Ala Gln Leu Leu Glu Gln Leu Gln Pro Leu Thr Glu Arg Tyr Ala Val
            355                 360                 365

Val Gly Glu Val Arg Gly Lys Gly Leu Met Ile Ala Val Asp Leu Val
            370                 375                 380

Ala Asp Lys Ala Thr Arg Glu Pro Leu Asp Pro Ala Thr Gly Leu Ala
385                 390                 395                 400

Ser Arg Ile Ala Glu Gln Ala Arg Arg Ala Gly Val Leu Met Arg Pro
            405                 410                 415

Ile Gly Asn Lys Ile Val Met Ser Pro Pro Leu Thr Leu Thr Ser Asp
            420                 425                 430

Glu Ala Ala Met Met Val Gly Ala Leu Asp Ser Ala Leu Ala Asp Cys
            435                 440                 445

Arg

<210> SEQ ID NO 2
<211> LENGTH: 1350
<212> TYPE: DNA
<213> ORGANISM: Pseudomonas sp.

<400> SEQUENCE: 2
atgtacgagc aatacaagac agcacaaaaa aaattctggc acccgatgag ttcttcggcg      60
ccggcgaacc gctccaagac gttgatcatc gcccgtggcg acggtaacta cgtcaccgat     120
atcgaaggcc atcgcatgct cgatggtgtc ggcggtttgt ggaacgtgaa cgtgggccat     180
aaccgggctt cagtgaaggc ggccattgcc gcgcagttgg acgaactggc ttattaccag     240
accttcgacg gcatcgccca tccgcgggtg ttcgacctcg ccgagcggct gacgtcgatg     300
ttcgcccagg aaaacatgac ccgggtgttg ttcagttccg gcggttccga tgcggtcgag     360
acggccctga aaatggcccg ccaatactgg atcgccagcg gcgagccagg acgcacgcgc     420
tttctctcat tgcgcaatgg ttaccatggc gtacacatgg gcggcacctc cgtgggcggc     480
aacggcgtgt atcactacaa ccacgggccg ctgttggcag gctgtcatct gctcgacacg     540
ccgtggctgt accgcaaccc ctgggactgc gcgatccag aggaactgac cgctcactgc      600
attcgtcagt ggaagacca gatcgcgctg ctcggcccgc agaccattgc cgcgctgatc      660
gccgaaccgg tgcaaggcgc cggcggcgtg atcgtgccgc cggcgtacta ctggaagggg     720
ctgcgcgaag tctgcgaccg ccacggcatc ctgttgatcg ccgatgaagt ggtgacgggt     780 ttcgccgta ccggttgcat gctcggcagt cgtggctggg gtgtcgcccc cgacgtactg      840
tgcctggcca agggtattac cgccggttac atccccatgg gcgccacagt cttcaaccag     900
cgcatggtcg atgccatcga aacggcccg ggcttcagca acgtaatcat gcacggctac      960
acctacagcg gacacccgac tgcctgtgcg gcggccctgg cggtgctgga catcgtcgag    1020
```

-continued

```
gccgaggatt tgccgggcaa cgccgggaaa atcggtgccc agttgctgga gcaactgcaa      1080
ccgttgaccg aacgttatgc ggtagtgggc gaagtgcgcg gcaagggctt gatgatcgcc      1140
gtggacctgg tggcagacaa ggccacgcgc gagccgcttg acccggctac gggcctggcc      1200
tcgcgcattg ccgagcaggc gcgccgcgcc ggcgtattga tgcgcccgat aggcaacaaa      1260
atcgtgatgt cgccaccgct gaccctcact tctgacgagg ccgccatgat ggtcggcgcg      1320
ttggacagcg cactcgctga ctgccgttag                                       1350

<210> SEQ ID NO 3
<211> LENGTH: 20
<212> TYPE: DNA
<213> ORGANISM: Artificial
<220> FEATURE:
<223> OTHER INFORMATION: primer1
<220> FEATURE:
<221> NAME/KEY: misc_feature
<222> LOCATION: (6)..(6)
<223> OTHER INFORMATION: n represents a, t, g or c
<220> FEATURE:
<221> NAME/KEY: misc_feature
<222> LOCATION: (9)..(9)
<223> OTHER INFORMATION: n represents a, t, g or c

<400> SEQUENCE: 3
aayacngtnc ayatgatgca                                                    20

<210> SEQ ID NO 4
<211> LENGTH: 20
<212> TYPE: DNA
<213> ORGANISM: Artificial
<220> FEATURE:
<223> OTHER INFORMATION: primer2
<220> FEATURE:
<221> NAME/KEY: misc_feature
<222> LOCATION: (12)..(12)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 4
acytgraara anccnggcat                                                    20

<210> SEQ ID NO 5
<211> LENGTH: 1365
<212> TYPE: DNA
<213> ORGANISM: Pseudomonas fluorescens

<400> SEQUENCE: 5
atgaacagca acaacaaagc ctggctcaaa gagcacaaca cggtgcacat gatgcatccg        60
atgcaggatc cgaaagcact gcacgaacag cgcccattga ttattcagtc cggtaagggc       120
gtacacatca ctgatgttga cgggcgtcgc ttcatcgatt gccagggcgg actatggtgc       180
gtcaatgccg gttacggtcg acgtgaaatc atcgacgcgg tgacccggca gatggaagag       240
ctggcgtact attcgttgtt tcccggcagc accaatgcgc cggccattgc gctttcgcag       300
aagttgaccg aggtggcggc cgaggagggc atggtcaagg catcgtttgg tctcggcggt       360
tcggacgccg tggagactgc gctgaaaatc gctcgtcaat actggaagct ggaaggccag       420
cccgacaagg tcaagttcgt ctcgttgtac aacggctatc acggcctgaa cttcggtggc       480
atgtccgcct gtggcggcaa cgcctggaaa agcagctacg aacccttgat gccgggcttc       540
ttccaggtcg aatcaccgca tctataccgc aaccctttca ccaatgatcc agaggaactc       600
```

-continued

```
gcagaaatct gtgcgcagat ccttgagcgg caaatcgaaa tgcaagcgcc gggcactgtc    660
gcggcgttga ttgccgagcc gatccaggga gctggcggag tcatcgtacc cccagcctct    720
tattggccgc gcttgcgcca gatctgcgac aagtatgaca ttctactgat cgccgatgag    780
gtcatcaccg gactgggtcg cagcggttcg ttgttcggtt cccgtggttg gggggtcaag    840
cccgacatca tgtgcctggc aaaaggtatc agcagcggtt atgtgcctct gagcgcgaca    900
ctggtcaact cccgcgtcgc ccgggcatgg gagcgtgatg ccggtttcac ctcggtctac    960
atgcatggct acacctattc cggtcaccct gtctcttgcg ccgctgcgct ggcggccatc   1020
gacatcgtgc tgcaggagaa tctcgccgaa aacgcacggg tggttggcga ctatttcctg   1080
gagaagctgc tgatactcaa ggacaaacat cgggccatcg gcgatgtgcg cggcaagggg   1140
ctgatgctgg cagtcgagct ggtcaaggaa agggcgacca aggagccgtt cggcccggca   1200
gacgcttatc cgctggccat ttccgaggcc tgtgtgaata acggagtgat gattcgtacc   1260
atcgtcaaca agctgatcat ctcgccgccg ttgaccttca ccaccgagca tgtcgacgaa   1320
gtgatcgagg tgctcgaccg cgccttcgtt gccaaccccct ggtaa               1365
```

<210> SEQ ID NO 6
<211> LENGTH: 454
<212> TYPE: PRT
<213> ORGANISM: Pseudomonas fluorescens

<400> SEQUENCE: 6

```
Met Asn Ser Asn Asn Lys Ala Trp Leu Lys Glu His Asn Thr Val His
 1               5                  10                  15

Met Met His Pro Met Gln Asp Pro Lys Ala Leu His Glu Gln Arg Pro
                20                  25                  30

Leu Ile Ile Gln Ser Gly Lys Gly Val His Ile Thr Asp Val Asp Gly
            35                  40                  45

Arg Arg Phe Ile Asp Cys Gln Gly Gly Leu Trp Cys Val Asn Ala Gly
        50                  55                  60

Tyr Gly Arg Arg Glu Ile Ile Asp Ala Val Thr Arg Gln Met Glu Glu
 65                  70                  75                  80

Leu Ala Tyr Tyr Ser Leu Phe Pro Gly Ser Thr Asn Ala Pro Ala Ile
                85                  90                  95

Ala Leu Ser Gln Lys Leu Thr Glu Val Ala Ala Glu Glu Gly Met Val
           100                 105                 110

Lys Ala Ser Phe Gly Leu Gly Gly Ser Asp Ala Val Glu Thr Ala Leu
        115                 120                 125

Lys Ile Ala Arg Gln Tyr Trp Lys Leu Glu Gly Gln Pro Asp Lys Val
    130                 135                 140

Lys Phe Val Ser Leu Tyr Asn Gly Tyr His Gly Leu Asn Phe Gly Gly
145                 150                 155                 160

Met Ser Ala Cys Gly Gly Asn Ala Trp Lys Ser Ser Tyr Glu Pro Leu
                165                 170                 175

Met Pro Gly Phe Phe Gln Val Glu Ser Pro His Leu Tyr Arg Asn Pro
            180                 185                 190

Phe Thr Asn Asp Pro Glu Glu Leu Ala Glu Ile Cys Ala Gln Ile Leu
        195                 200                 205

Glu Arg Gln Ile Glu Met Gln Ala Pro Gly Thr Val Ala Ala Leu Ile
    210                 215                 220

Ala Glu Pro Ile Gln Gly Ala Gly Gly Val Ile Val Pro Pro Ala Ser
225                 230                 235                 240

Tyr Trp Pro Arg Leu Arg Gln Ile Cys Asp Lys Tyr Asp Ile Leu Leu
```

```
            245                 250                 255
Ile Ala Asp Glu Val Ile Thr Gly Leu Gly Arg Ser Gly Ser Leu Phe
            260                 265                 270

Gly Ser Arg Gly Trp Gly Val Lys Pro Asp Ile Met Cys Leu Ala Lys
        275                 280                 285

Gly Ile Ser Ser Gly Tyr Val Pro Leu Ser Ala Thr Leu Val Asn Ser
    290                 295                 300

Arg Val Ala Arg Ala Trp Glu Arg Asp Ala Gly Phe Thr Ser Val Tyr
305                 310                 315                 320

Met His Gly Tyr Thr Tyr Ser Gly His Pro Val Ser Cys Ala Ala Ala
                325                 330                 335

Leu Ala Ala Ile Asp Ile Val Leu Gln Glu Asn Leu Ala Glu Asn Ala
            340                 345                 350

Arg Val Val Gly Asp Tyr Phe Leu Glu Lys Leu Leu Ile Leu Lys Asp
        355                 360                 365

Lys His Arg Ala Ile Gly Asp Val Arg Gly Lys Gly Leu Met Leu Ala
    370                 375                 380

Val Glu Leu Val Lys Glu Arg Ala Thr Lys Glu Pro Phe Gly Pro Ala
385                 390                 395                 400

Asp Ala Tyr Pro Leu Ala Ile Ser Glu Ala Cys Val Asn Asn Gly Val
                405                 410                 415

Met Ile Arg Thr Ile Val Asn Lys Leu Ile Ile Ser Pro Pro Leu Thr
            420                 425                 430

Phe Thr Thr Glu His Val Asp Glu Val Ile Glu Val Leu Asp Arg Ala
        435                 440                 445

Phe Val Ala Asn Pro Trp
    450

<210> SEQ ID NO 7
<211> LENGTH: 33
<212> TYPE: DNA
<213> ORGANISM: Artificial
<220> FEATURE:
<223> OTHER INFORMATION: primer3

<400> SEQUENCE: 7
tggagtggcc atatgaacag ccaacaacaa agc                             33

<210> SEQ ID NO 8
<211> LENGTH: 33
<212> TYPE: DNA
<213> ORGANISM: Artificial
<220> FEATURE:
<223> OTHER INFORMATION: primer4

<400> SEQUENCE: 8
tggtcagcga attcttacca ggggttggca acg                             33

<210> SEQ ID NO 9
<211> LENGTH: 23
<212> TYPE: DNA
<213> ORGANISM: Artificial
<220> FEATURE:
<223> OTHER INFORMATION: primer5
<220> FEATURE:
<221> NAME/KEY: misc_feature
<222> LOCATION: (3)..(3)
<223> OTHER INFORMATION: n represents a, t, g or c

<400> SEQUENCE: 9
gcngtyttrt aytgytcrta cat                                        23
```

```
<210> SEQ ID NO 10
<211> LENGTH: 23
<212> TYPE: DNA
<213> ORGANISM: Artificial
<220> FEATURE:
<223> OTHER INFORMATION: primer6
<220> FEATURE:
<221> NAME/KEY: misc_feature
<222> LOCATION: (20)..(20)
<223> OTHER INFORMATION: n represents a, t, g or c

<400> SEQUENCE: 10
araaraartt ytggcayccn atg                                              23

<210> SEQ ID NO 11
<211> LENGTH: 45
<212> TYPE: DNA
<213> ORGANISM: Artificial
<220> FEATURE:
<223> OTHER INFORMATION: primer7

<400> SEQUENCE: 11
acagagtgag gagtgcacat atgtacgagc aatacaagac agcac                      45

<210> SEQ ID NO 12
<211> LENGTH: 45
<212> TYPE: DNA
<213> ORGANISM: Artificial
<220> FEATURE:
<223> OTHER INFORMATION: primer8

<400> SEQUENCE: 12
aatagagctc ttactaacgg cagtcagcga gtgcgctgtc caacg                      45

<210> SEQ ID NO 13
<211> LENGTH: 44
<212> TYPE: DNA
<213> ORGANISM: Artificial
<220> FEATURE:
<223> OTHER INFORMATION: primer9

<400> SEQUENCE: 13
agggaaacag catatggcat tcagcgccga tacctccgag atcg                       44

<210> SEQ ID NO 14
<211> LENGTH: 51
<212> TYPE: DNA
<213> ORGANISM: Artificial
<220> FEATURE:
<223> OTHER INFORMATION: primer10

<400> SEQUENCE: 14
atagagctct tatcagtact gcacaggagt aagcaaagaa gagctttcga c               51

<210> SEQ ID NO 15
<211> LENGTH: 32
<212> TYPE: DNA
<213> ORGANISM: Artificial
<220> FEATURE:
<223> OTHER INFORMATION: primer11

<400> SEQUENCE: 15
gccgaattct aaggaggtta acaatgtata aa                                    32

<210> SEQ ID NO 16
<211> LENGTH: 28
```

```
<212> TYPE: DNA
<213> ORGANISM: Artificial
<220> FEATURE:
<223> OTHER INFORMATION: primer12

<400> SEQUENCE: 16
gcggtcgact tatccgcgtc ctgcttgg                                        28

<210> SEQ ID NO 17
<211> LENGTH: 20
<212> TYPE: DNA
<213> ORGANISM: Artificial
<220> FEATURE:
<223> OTHER INFORMATION: primer13
<220> FEATURE:
<221> NAME/KEY: misc_feature
<222> LOCATION: (3)..(3)
<223> OTHER INFORMATION: n represents a, t, g or c
<220> FEATURE:
<221> NAME/KEY: misc_feature
<222> LOCATION: (9)..(9)
<223> OTHER INFORMATION: n represents a, t, g or c
<220> FEATURE:
<221> NAME/KEY: misc_feature
<222> LOCATION: (12)..(12)
<223> OTHER INFORMATION: n represents a, t, g or c

<400> SEQUENCE: 17
acntaygcna cntggaaryt                                                 20

<210> SEQ ID NO 18
<211> LENGTH: 20
<212> TYPE: DNA
<213> ORGANISM: Artificial
<220> FEATURE:
<223> OTHER INFORMATION: primer14
<220> FEATURE:
<221> NAME/KEY: misc_feature
<222> LOCATION: (9)..(9)
<223> OTHER INFORMATION: n represents a, t, g or c
<220> FEATURE:
<221> NAME/KEY: misc_feature
<222> LOCATION: (12)..(12)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 18
ccrtaraang tngcnccytt                                                 20

<210> SEQ ID NO 19
<211> LENGTH: 972
<212> TYPE: DNA
<213> ORGANISM: Pediococcus acidilactici

<400> SEQUENCE: 19
atgtctaata ttcaaaatca tcaaaaagtt gtcctcgtcg gtgacggtgc cgtaggttct     60
agttacgcat tcgcgatggc acaacaagga atcgctgaag aattcgtcat tgtcgacgtt    120
gttaaggatc gtacagttgg ggacgcattg gaccttgaag atgctactcc attcacagct    180
ccaaagaaca tctactctgg tgaatactca gactgcaagg atgctgactt agttgttatc    240
acagctggcg caccacaaaa gccaggtgaa acacgtcttg accttgttaa caagaactta    300
aacatccttt caacaattgt taaaccagtt gttgattctg gttttgatgg tatcttcctt    360
gttgctgcta acccagttga tatccttact tacgcaacat ggaaattctc tggcttccct    420
aaggaaaaag ttatcggttc aggtatctca cttgacacag ctcgtttgcg cgtagctctt    480
```

-continued

```
ggtaagaaat tcaacgttag cccagaatct gtagatgctt acatcttagg tgaacatggt    540
gacagtgaat ttgctgcttt ctcatcagct acaatcggta caaagccatt gcttgaaatc    600
gctaaagaag aaggcgtttc aactgacgaa ttggctgaaa tcgaagacag cgtacgtaac    660
aaagcttatg aaatcatcaa caagaagggt gctacattct acggtgttgg tactgcattg    720
atgcgcattt ctaaagcaat tcttcgcgac gaaaacgccg tattgcctgt gggcgcatac    780
atggacggcg aatatggttt gaacgacatt tacattggta ctcctgcagt tatcaatggt    840
caaggtctaa accgcgttat cgaagcacca cttagcgatg acgaaaagaa gaagatgact    900
gactcagcaa ctactttgaa gaaggttctt actgacggtc taaacgctct tgctgaaaaa    960
caagacaaat aa                                                        972
```

<210> SEQ ID NO 20
<211> LENGTH: 323
<212> TYPE: PRT
<213> ORGANISM: Pediococcus acidilactici

<400> SEQUENCE: 20

```
Met Ser Asn Ile Gln Asn His Gln Lys Val Val Leu Val Gly Asp Gly
 1               5                  10                  15

Ala Val Gly Ser Ser Tyr Ala Phe Ala Met Ala Gln Gln Gly Ile Ala
            20                  25                  30

Glu Glu Phe Val Ile Val Asp Val Lys Asp Arg Thr Val Gly Asp
        35                  40                  45

Ala Leu Asp Leu Glu Asp Ala Thr Pro Phe Thr Ala Pro Lys Asn Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Thr Arg Leu Asp Leu Val
                85                  90                  95

Asn Lys Asn Leu Asn Ile Leu Ser Thr Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Glu Lys Val
    130                 135                 140

Ile Gly Ser Gly Ile Ser Leu Asp Thr Ala Arg Leu Arg Val Ala Leu
145                 150                 155                 160

Gly Lys Lys Phe Asn Val Ser Pro Glu Ser Val Asp Ala Tyr Ile Leu
                165                 170                 175

Gly Glu His Gly Asp Ser Glu Phe Ala Ala Phe Ser Ser Ala Thr Ile
            180                 185                 190

Gly Thr Lys Pro Leu Leu Glu Ile Ala Lys Glu Glu Gly Val Ser Thr
        195                 200                 205

Asp Glu Leu Ala Glu Ile Glu Asp Ser Val Arg Asn Lys Ala Tyr Glu
    210                 215                 220

Ile Ile Asn Lys Lys Gly Ala Thr Phe Tyr Gly Val Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Glu Tyr Gly Leu Asn Asp Ile Tyr Ile
            260                 265                 270

Gly Thr Pro Ala Val Ile Asn Gly Gln Gly Leu Asn Arg Val Ile Glu
        275                 280                 285
```

-continued

```
Ala Pro Leu Ser Asp Asp Glu Lys Lys Lys Met Thr Asp Ser Ala Thr
        290                 295                 300

Thr Leu Lys Lys Val Leu Thr Asp Gly Leu Asn Ala Leu Ala Glu Lys
305                 310                 315                 320

Gln Asp Lys
```

<210> SEQ ID NO 21
<211> LENGTH: 34
<212> TYPE: DNA
<213> ORGANISM: Artificial
<220> FEATURE:
<223> OTHER INFORMATION: primer15

<400> SEQUENCE: 21
gggaatggac atatgtctaa tattcaaaat catc          34

<210> SEQ ID NO 22
<211> LENGTH: 40
<212> TYPE: DNA
<213> ORGANISM: Artificial
<220> FEATURE:
<223> OTHER INFORMATION: primer16

<400> SEQUENCE: 22
gataagaatt cttattattt gtcttgtttt tcagcaagag          40

<210> SEQ ID NO 23
<211> LENGTH: 45
<212> TYPE: DNA
<213> ORGANISM: Artificial
<220> FEATURE:
<223> OTHER INFORMATION: primer17

<400> SEQUENCE: 23
aatgagctct aaggaggtta acaatgtcta atattcaaaa tcatc          45

<210> SEQ ID NO 24
<211> LENGTH: 41
<212> TYPE: DNA
<213> ORGANISM: Artificial
<220> FEATURE:
<223> OTHER INFORMATION: primer18

<400> SEQUENCE: 24
aattgcatgc ttattatccg cgtcctgctt ggaatgatgg g          41

<210> SEQ ID NO 25
<211> LENGTH: 330
<212> TYPE: PRT
<213> ORGANISM: Arthrobacter sp.

<400> SEQUENCE: 25

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80
```

```
Asp Asp His Ile Glu Arg Leu Phe Ser Asn Ala Glu Ser Met Arg Ile
            85                  90                  95
Ile Pro Pro Leu Thr Gln Asp Glu Val Lys Glu Ile Ala Leu Glu Leu
           100                 105                 110
Val Ala Lys Thr Glu Leu Arg Glu Ala Phe Val Ser Val Ser Ile Thr
       115                 120                 125
Arg Gly Tyr Ser Ser Thr Pro Gly Glu Arg Asp Ile Thr Lys His Arg
   130                 135                 140
Pro Gln Val Tyr Met Tyr Ala Val Pro Tyr Gln Trp Ile Val Pro Phe
145                 150                 155                 160
Asp Arg Ile Arg Asp Gly Val His Ala Met Val Ala Gln Ser Val Arg
               165                 170                 175
Arg Thr Pro Arg Ser Ser Ile Asp Pro Gln Val Lys Asn Phe Gln Trp
           180                 185                 190
Gly Asp Leu Ile Arg Ala Val Gln Glu Thr His Asp Arg Gly Phe Glu
       195                 200                 205
Ala Pro Leu Leu Leu Asp Gly Asp Gly Leu Leu Ala Glu Gly Ser Gly
   210                 215                 220
Phe Asn Val Val Ile Lys Asp Gly Val Val Arg Ser Pro Gly Arg
225                 230                 235                 240
Ala Ala Leu Pro Gly Ile Thr Arg Lys Thr Val Leu Glu Ile Ala Glu
               245                 250                 255
Ser Leu Gly His Glu Ala Ile Leu Ala Asp Ile Thr Leu Ala Glu Leu
           260                 265                 270
Leu Asp Ala Asp Glu Val Leu Gly Cys Thr Thr Ala Gly Gly Val Trp
       275                 280                 285
Pro Phe Val Ser Val Asp Gly Asn Pro Ile Ser Asp Gly Val Pro Gly
   290                 295                 300
Pro Ile Thr Gln Ser Ile Ile Arg Arg Tyr Trp Glu Leu Asn Val Glu
305                 310                 315                 320
Ser Ser Ser Leu Leu Thr Pro Val Gln Tyr
               325                 330

<210> SEQ ID NO 26
<211> LENGTH: 993
<212> TYPE: DNA
<213> ORGANISM: Arthrobacter sp.

<400> SEQUENCE: 26
```

| | | | | | |
|---|---|---|---|---|---|
| atggcattca | gcgccgatac | ctccgagatc | gtctacacgc | acgacaccgg | cctcgactac | 60 |
| atcacttata | gcgactacga | actcgatcct | gctaacccgc | tcgcgggagg | tgcggcatgg | 120 |
| atcgagggtg | cattcgtgcc | gccgtcggag | gcgcggatct | cgatcttcga | tcagggttac | 180 |
| ctccactcgg | acgtcaccta | cacggtcttc | cacgtctgga | acggaaatgc | attccgcctc | 240 |
| gacgaccaca | tcgaacgcct | cttctccaac | gcggagtcga | tgcgcatcat | ccctccgctc | 300 |
| acacaggacg | aagtgaagga | gattgcgctc | gaactcgtcg | cgaagaccga | attgcgtgag | 360 |
| gccttcgtgt | ccgtgtcgat | tacccgcggt | tacagctcga | ctccgggcga | gcgcgacatc | 420 |
| acgaagcacc | gcccgcaggt | gtacatgtat | gccgtcccat | atcagtggat | cgtgccgttt | 480 |
| gaccgaattc | gcgacggcgt | gcacgccatg | gtcgcacaga | gcgtgcgccg | aaccccgcgc | 540 |
| agctcgatcg | accctcaggt | caagaacttc | cagtgggggg | atctgatccg | tgcggttcaa | 600 |
| gagacgcacg | accgcgggtt | cgaggctccc | cttctgctcg | acggcgatgg | actgcttgcc | 660 |
| gagggctcgg | ggttcaacgt | cgtcgtgatc | aaggacggcg | tcgtgcgcag | cccgggtcga | 720 |

```
gcggcgctcc ccggcattac gcggaagacc gtgctcgaga tcgccgaatc gctcggacac      780
gaggcgattc tcgccgacat cacgctcgct gaactgctcg acgccgacga agtgctcggc      840
tgcacgactg cgggcggagt gtggccattc gtcagcgtgg acgcaaccc catctcggac      900 ggggttcccg gccccatcac ccagtcgatc atccgtcgtt actgggagct gaatgtcgaa      960
agctcttctt tgcttactcc tgtgcagtac tga                                   993
```

```
<210> SEQ ID NO 27
<211> LENGTH: 32
<212> TYPE: DNA
<213> ORGANISM: Artificial
<220> FEATURE:
<223> OTHER INFORMATION: primer19

<400> SEQUENCE: 27
accaccggta cctaaggagg ttaacaatgg cg                                     32
```

```
<210> SEQ ID NO 28
<211> LENGTH: 31
<212> TYPE: DNA
<213> ORGANISM: Artificial
<220> FEATURE:
<223> OTHER INFORMATION: primer20

<400> SEQUENCE: 28
ccaccagcat gctcagccgg ccttcttgaa c                                      31
```

```
<210> SEQ ID NO 29
<211> LENGTH: 30
<212> TYPE: DNA
<213> ORGANISM: Artificial
<220> FEATURE:
<223> OTHER INFORMATION: primer21

<400> SEQUENCE: 29
ccaccaccca tatgtctaat attcaaaatc                                        30
```

```
<210> SEQ ID NO 30
<211> LENGTH: 30
<212> TYPE: DNA
<213> ORGANISM: Artificial
<220> FEATURE:
<223> OTHER INFORMATION: primer22

<400> SEQUENCE: 30
caccaccaaa taccttattt gtcttgtttt                                        30
```

```
<210> SEQ ID NO 31
<211> LENGTH: 32
<212> TYPE: DNA
<213> ORGANISM: Artificial
<220> FEATURE:
<223> OTHER INFORMATION: primer23

<400> SEQUENCE: 31
accaccggta cctaaggagg ttaacaatgg cg                                     32
```